United States Patent
Zhang et al.

(10) Patent No.: US 10,324,152 B2
(45) Date of Patent: Jun. 18, 2019

(54) APPARATUS FOR IMPROVING MAGNETIC RESONANCE IMAGING

(71) Applicant: Trustees of Boston University, Boston, MA (US)

(72) Inventors: Xin Zhang, Medford, MA (US); Stephan Anderson, Boston, MA (US); Guangwu Duan, Natick, MA (US); Xiaoguang Zhao, Boston, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 16/002,458

(22) Filed: Jun. 7, 2018

(65) Prior Publication Data

US 2018/0356483 A1 Dec. 13, 2018

Related U.S. Application Data

(60) Provisional application No. 62/516,376, filed on Jun. 7, 2017.

(51) Int. Cl.
  *G01V 3/00* (2006.01)
  *G01R 33/56* (2006.01)
  (Continued)

(52) U.S. Cl.
  CPC .......... *G01R 33/5608* (2013.01); *A61B 5/055* (2013.01); *G01R 33/343* (2013.01); *G01R 33/3628* (2013.01)

(58) Field of Classification Search
  CPC ..................................................... G01R 33/343
  (Continued)

(56) References Cited

U.S. PATENT DOCUMENTS

| 5,489,847 A | 2/1996 | Nabeshima et al. |
| 6,002,311 A | 12/1999 | Wey et al. |

(Continued)

FOREIGN PATENT DOCUMENTS

| WO | WO 2016/011227 A1 | 1/2016 |
| WO | WO 2017/017181 A1 | 2/2017 |

OTHER PUBLICATIONS

Aydin, K., et al., "Investigation of Magnetic Resonance for Different Split-Ring Resonator Parameters and Designs," *New Journal of Physics*, vol. 7, Issue 1, 15 pages, 2005.

(Continued)

*Primary Examiner* — Louis M Arana
(74) *Attorney, Agent, or Firm* — Nutter McClennen & Fish LLP

(57) ABSTRACT

A passive apparatus including a plurality of resonators increases signal-to-noise ratio of radiofrequency signals emitted by a specimen and captured by an MRI machine. The apparatus increases the magnetic field component of radiofrequency energy during signal transmission from the MRI machine to the specimen, and/or reception of signals from the specimen to the MRI machine. Moreover, the apparatus enhances specimen safety by substantially avoiding unwanted generation of an electric field, or an increase in the electric field component of the RF energy. Use of the apparatus improves the images generated by the MRI machine, and/or reduces the time necessary for the MRI machine to capture the image.

20 Claims, 17 Drawing Sheets

(51) Int. Cl.
    G01R 33/36     (2006.01)
    G01R 33/343    (2006.01)
    A61B 5/055     (2006.01)
(58) Field of Classification Search
    USPC .................................................. 324/318, 322
    See application file for complete search history.

(56)        References Cited

U.S. PATENT DOCUMENTS 7,176,840 B1    2/2007  Kelley
    7,945,322 B2    5/2011  Stevenson et al.
    8,159,223 B2*   4/2012  Luekeke ............... G01R 33/341
                                                        324/318
    10,031,192 B2*  7/2018  Fackelmeier ........ G01R 33/341
    2003/0028095 A1 2/2003  Tulley et al.
    2010/0127707 A1* 5/2010 Lee .................. G01R 33/34007
                                                        324/318
    2011/0204891 A1 8/2011  Drake et al.
    2015/0015259 A1 1/2015  Duan et al.
    2016/0033592 A1 2/2016  Demir et al.

OTHER PUBLICATIONS

By, S., et al., "A 16-Channel Receive, Forced Current Excitation Dual-Transmit Coil for Breast Imaging at 7T," *PLOS One*, pp. 1-16, Nov. 24, 2014.
Darnell, A., et al., "Liver Imaging Reporting and Data System with MR Imaging: Evaluation in Nodules 20 mm or Smaller Detected in Cirrhosis at Screening US," *Radiology*, vol. 275, No. 3, pp. 698-707, Jun. 2015.
Duke, E., et al., "A Systemactic Review and Meta-Analysis of Diagnostic Performance of MRI for Evaluation of Acute Appendicitis," *AJR Am. J. Roentgenol.*, vol. 206, No. 3, pp. 508-517, Mar. 2016.
Freire, M., et al., "Experimental Demonstration of a µ=-1 Metamaterial Lens for Magnetic Resonance Imaging,"*Appl. Phys. Lett.*, vol. 93, Issue 23, 12 pages, Nov. 2008.
Freire, M., et al., "On the Applications of $\mu_r$=-1 Metamaterial Lenses for Magnetic Resonance Imaging," *Journal of Magnetic Resonance*, vol. 203, Issue 1, pp. 81-90, Mar. 2010.
Hawkes, A., et al., "A Microwave Metamaterial with Integrated Power Harvesting Functionality," *Applied Physics Letters*, vol. 103, Issue 16, 4 pages, Sep. 2013.
Kollia, K., et al., "First Clinical Study on Ultra-High-Field MR Imaging in Patients with Multiple Sclerosis: Comparison of 1.5T and 7T," *Am. J. of Neuroradiology*, vol. 30, Issue 4, pp. 699-702, Apr. 2009.
Le Bihan, D., et al., "Diffusion Magnetic Resonance Imaging: What Water Tells Us About Biological Tissues," *PLOS Biology*, pp. 1-13, Jul. 23, 2015.
Marqués, R., et al., "Left-Handed-Media Simulation and Transmission of EM Waves in Subwavelength Split-Ring-Resonator-Loaded Metallic Waveguides," *Physical Review Letters*, vol. 89, No. 18, 4 pages, Oct. 28, 2002.
Mazaheri, Y., et al., "Image Artifacts on Prostate Diffusion-Weighted Magnetic Resonance Imaging: Trade-offs at 1.5 Tesla and 3.0 Tesla," *Academic Radiology*, vol. 20, No. 8, pp. 1042-1047, Aug. 2013.
Nguyen, F., et al., "MR Imaging-Based Diagnosis and Classification of Meniscal Tears," *RadioGraphics*, vol. 34, Issue 4, pp. 981-999, Jul.-Aug. 2014.
Pendry, J.B., et al. "Magnetism from Conductors and Enhanced Nonlinear Phenomena," *IEEE Transactions on Microwave Theory and Techniques*, vol. 47, No. 11, pp. 2075-2084, Nov. 1999.

Radu, X., et al., "Toward a Wire Medium Endoscope for MRI Imaging," *Metamaterials*, vol. 3, Issue 2, pp. 90-99, Oct. 2009.
Riascos, R., et al., "Imaging of Atlanto-Occipital and Atlantoaxial Traumatic Injuries: What the Radiologist Needs to Know," *RadioGraphics*, vol. 35, Issue 7, pp. 2121-2134, Nov.-Dec. 2015.
Robinson, S., et al., "Combining Phase Images from Multi-Channel RF Coils Using 3D Phase Offset Maps Derived from a Dual-Echo Scan," *Magnetic Resonance in Medicine*, vol. 65, No. 6, pp. 1638-1648, Jun. 2011.
Shelby, R.A., et al., "Experimental Verification of a Negative Index of Refraction," *Science*, vol. 292, Issue 5514, pp. 77-79, Apr. 6, 2001.
Slobozhanyuk, A., et al., "Enhancement of Magnetic Resonance Imaging with Metasurfaces," *Advanced Materials*, 22 pages, 2016.
Slobozhanyuk, A., et al., "Enhancement of Magnetic Resonance Imaging with Metasurfaces," *Physics.Med-Ph*, 6 pages, Jul. 6, 2015.
Slobozhanyuk, A., et al., Enhancement of Magnetic Resonance Imaging with Metasurfaces, *Advanced Materials*, vol. 28, pp. 1832-1838, 2016.
Stahl, R., et al., "Assessment of Cartilage-Dedicated Sequences at Ultra-High-Field MRI: Comparison of Imaging Performance and Diagnostic Confidence Between 3.0 and 7.0 T with Respect to Osteoarthritis-Induced Changes at the Knee Joint," *Skeletal Radiol.*, vol. 38, pp. 771-783, 2009.
Syms, R.R.A., et al., "Flexible Magnetoinductive Ring MRI Detector: Design for Invariant Nearest-Neighbour Coupling," *Metamaterials*, vol. 4, Issue 1, pp. 1-14, May 2010.
Tao, H., et al., "MEMS Based Structurally Tunable Metamaterials at Terahertz Frequencies," *Journal of Infrared, Millimeter and Terahertz Waves*, vol. 32, Issue 5, pp. 580-595, May 2011.
Tao, H, et al., "Metamaterials on Paper as a Sensing Platform," *Advanced Materials*, vol. 23, Issue 28, pp. 3197-3201, Jul. 26, 2011.
Tao, H., et al., "Microwave and Terahertz Wave Sensing With Metamaterials," *Optics Express*, vol. 19, No. 22, 7 pages, Oct. 24, 2011.
Tolouee, A., et al., "Compressed Sensing Reconstruction of Cardiac Cine MRI Using Golden Angle Spiral Trajectories," *Journal of Magnetic Resonance*, vol. 260, pp. 10-19, Nov. 2015.
Veselago, V.G., "The Electrodynamics of Substances with Simultaneously Negative Values of $\epsilon$ and $\mu$," *Soviet Physics Uspekhi*, vol. 10, No. 4, pp. 509-514, Jan.-Feb. 1968.
Weintraub, M., et al., "Biologic Effects of 3 Tesla (T) MR Imaging Comparing Traditional 1.5 T and 0.6 T in 1023 Consecutive Outpatients," *American Society of Neuroimaging*, vol. 17, Issue 3, pp. 241-245, Jul. 2007.
Wiltshire, M.C.K., et al., "Microstructured Magnetic Materials for RF Flux Guides in Magnetic Resonance Imaging," *Science*, vol. 291, Issue 5505, pp. 849-851, Feb. 2, 2001.
Wiltshire, M.C.K., et al., "Microstructured Magnetic Materials for Radio Frequency Operation in Magnetic Resonance Imaging (MRI)," *MRI Paper Final*, 10 pages, filed on Dec. 10, 2000.
Zhao, X., et al., "Optically Tunable Metamaterial Perfect Absorber on Highly Flexible Substrate," *Sensors and Actuators A: Physical*, vol. 231, pp. 74-80, Jul. 15, 2015.
International Searching Authority, Notification of Transmittal of the International Search Report and the Written Opinion of the International Searching Authority, or the Declaration, PCT/US18/36447, 19 pages, dated Aug. 30, 2018.
Poutrina E., et al., "Analysis of nonlinear electromagnetic metamaterials," New Journal of Physics, vol. 12, 28 pages (2010).
Shadrivov H.V., et al., "Nonlinear magnetic metamaterials," Optics Express, vol. 16, Issue No. 25, pp. 20266-20271 (Dec. 2008).
Wang B., "Nonlinear properties of split-ring resonators," Optics Express, vol. 16, Issue No. 20, pp. 16058-16063 (Sep. 2008).

* cited by examiner

| Signal Strength (Mean) | | | | |
|---|---|---|---|---|
| 1 | 2 | 3 | 4 | |
| 157.2 | 173.2 | 178.5 | 178.1 | |
| 5 | 6 | 7 | 8 | 9 |
| 158.5 | 166.3 | 172.3 | 151.3 | 184.8 |

| Noise Level (StdDev) | | |
|---|---|---|
| 10 | 11 | 12 | Avrg |
| 4.4 | 4.6 | 5.2 | 4.7 |

| SNR | | | | |
|---|---|---|---|---|
| 1 | 2 | 3 | 4 | |
| 33.2 | 36.6 | 37.7 | 37.6 | |
| 5 | 6 | 7 | 8 | 9 |
| 33.5 | 35.1 | 36.4 | 32.0 | 39.0 |

Signal Strength (Mean):

| 1 | 2 | 3 | 4 | |
|---|---|---|---|---|
| 1174 | 640.4 | 546.6 | 481.1 | |
| 5 | 6 | 7 | 8 | 9 |
| 193.1 | 404.5 | 428.6 | 267.6 | 289.7 |

Noise level (StdDev):

| 10 | 11 | 12 | Avrg |
|---|---|---|---|
| 4.1 | 4.7 | 3.9 | 4.2 |

SNR

| 1 | 2 | 3 | 4 | |
|---|---|---|---|---|
| 277.3 | 151.3 | 129.1 | 113.6 | |
| 5 | 6 | 7 | 8 | 9 |
| 45.6 | 95.5 | 101.2 | 63.2 | 68.4 |

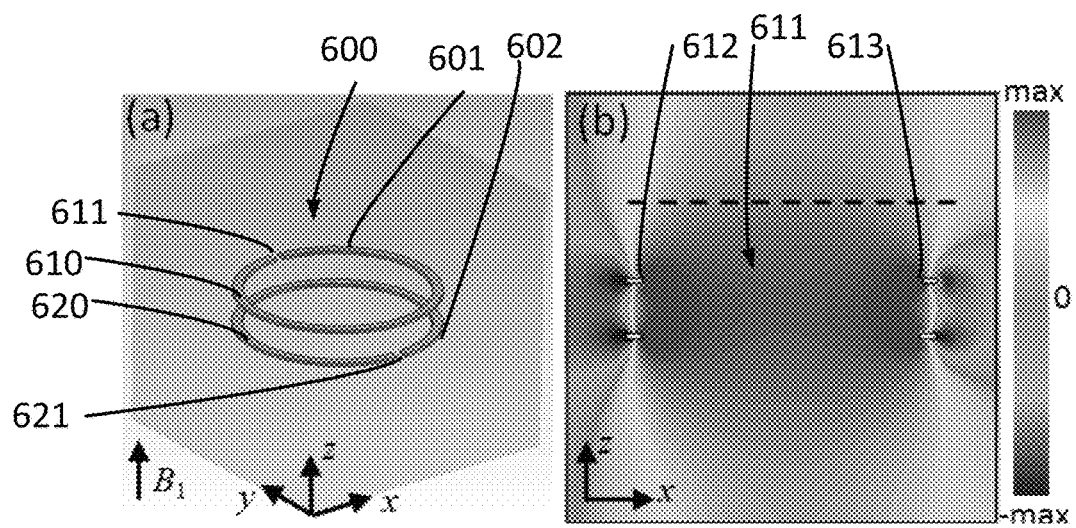
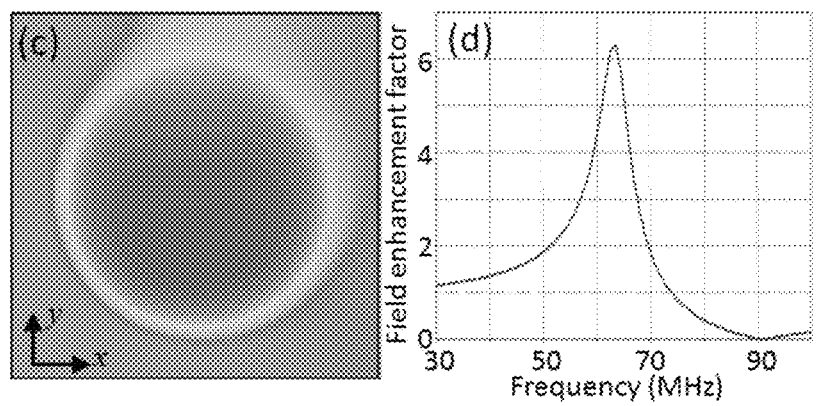
Fig. 6A Fig. 6B
Fig. 6C Fig. 6D
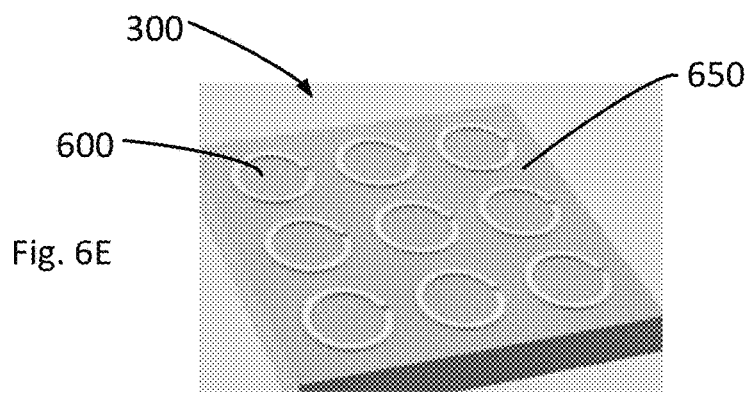
Fig. 6E

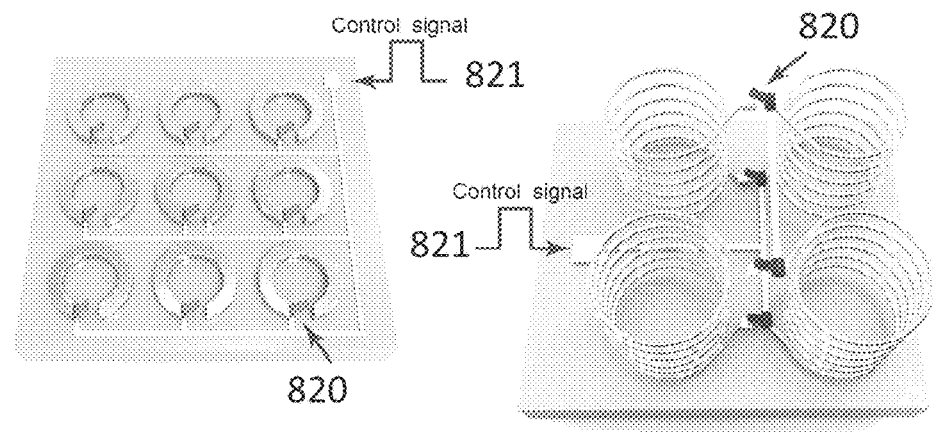
Fig. 8D
Fig. 8E
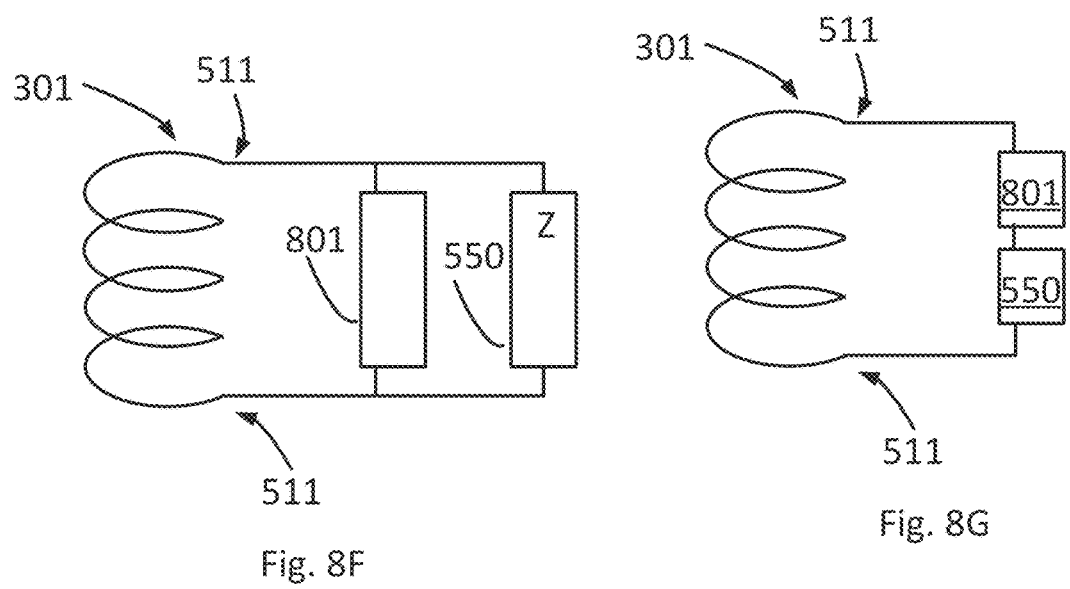
Fig. 8F
Fig. 8G

APPARATUS FOR IMPROVING MAGNETIC RESONANCE IMAGING

TECHNICAL FIELD

This patent application claims priority from provisional U.S. patent application No. 62/516,376, filed Jun. 7, 2017, entitled, "Apparatus for Improving Magnetic Resonance Imaging," and naming Xin Zhang, Stephan Anderson, Guangwu Duan, and Xiaoguang Zhao as inventors [practitioner's file 3273/119], the disclosure of which is incorporated herein, in its entirety, by reference.

TECHNICAL FIELD

The present invention relates to medical imaging, and more particularly to magnetic resonance imaging.

BACKGROUND ART

Magnetic resonance imaging ("MRI") is a medical imaging technique that captures an image of a specimen's internal structures without the use of X-rays. An MRI machine applies a strong magnetic field and electromagnetic stimulus to the specimen, causing atoms of the specimen to emit electromagnetic signals in response. The MRI machine captures the electromagnetic signals emitted by the specimen and from those captured signals constructs the image.

A known limitation of MRI machines is the signal-to-noise ratio (SNR) of the captured signals. Noise is generated by a variety of sources, including the circuitry of the MRI machine itself, and corrupts and obscures the signals emitted by the specimen. SNR may be improved by either boosting the signal, for example by increasing the strength of the static magnetic field, or by reducing the noise, for example by improving the MRI machine's signal processing circuitry, or by a combination of both. Such approaches are less than ideal, however, there are limits to the amount of power that can be safely applied to some specimens, such as a living animal, and noise cannot be completely eliminated.

SUMMARY OF VARIOUS EMBODIMENTS

In accordance with illustrative embodiments, an apparatus includes a plurality of resonators, and operates to increase the signal-to-noise ratio of radiofrequency signals emitted by a patient and captured by an MRI machine.

In an illustrative embodiment, the apparatus includes an array of resonators (each resonator is a "unit cell") configured to resonate at the working frequency. The array is configured to be disposed within the bore of an MRI machine, along with a specimen in the bore, when the MRI machine is imaging the specimen. In operation, the array increases the signal-to-noise ratio of the signals measured by the MRI machine.

In some embodiments, the apparatus has a resonance frequency different from the working frequency of the MRI machine. Indeed, in some embodiments the apparatus has a resonance frequency that can be tuned by changing the spacing between the resonators of the array.

In some embodiments, each resonator is a broadside-coupled split-ring resonator. In other embodiments, each resonator is an open-loop coil, and may be a helical coil. In general, each of the resonators is configured to couple with and amplify the magnetic field of the signal, but not couple with the electric field of the signal.

An illustrative embodiment provides an apparatus for improving operation of an MRI machine, the MRI machine characterized by a working frequency, by improving the signal-to-noise ratio of signals received by the MRI machine. The apparatus includes an array of unit cells, the array sized to be (or configured to be) disposed within a bore of the MRI machine along with a specimen in the bore, when the MRI machine is imaging the specimen. Each unit cell has a resonant frequency, and the array has a resonance frequency at or near the working frequency of the MRI machine (for example, in some embodiments the array has a resonance frequency with +/−5% (inclusive) of the working frequency of the MRI machine). The unit cells are configured such that they couple with one another (e.g., magnetically couple with one another), the array producing, in the signals measured by the MRI machine, a signal-to-noise ratio of at least 50. In some embodiments, the unit cells are low-dielectric constant resonators. In preferred embodiments, the unit cells are configured to amplify the magnetic field of the signal, but not amplify the electric field of the signal.

In some embodiments, each unit cell includes a broadside-coupled split-ring resonator.

In other embodiments, the unit cells are open-loop coils, and in preferred embodiments are helical coils. In preferred embodiments, the array is configured such that its resonance frequency can be tuned by changing the spacing between the unit cells. In preferred embodiments, the unit cell includes a core, and an open-loop coil wound around the core. In some such embodiments, the core has a relative permittivity of between 80 and 173, and in some embodiments the core is made of titanium dioxide.

In some embodiments, the resonance frequency of the array is different from the working frequency of the MRI machine.

In some embodiments, each unit cell includes a coil having two ends, and each unit cell further includes a capacitor electrically coupled between the two ends. In other embodiments, each unit cell includes an inductor electrically coupled between the two ends.

In illustrative embodiments, each unit cell includes a coil having two ends, and a coupler having a controllable variable impedance coupled between the two ends. Such unit cells have a first resonant frequency when the coupler is in a first impedance state, and a second resonant frequency when the coupler is in a second impedance state. In illustrative embodiments, the coupler is a semiconductor patch configured to change from the first impedance state to the second impedance state in response to RF energy transmitted by the MRI machine, to shift the resonant frequency of the unit cell away from the working frequency of the MRI machine such that the unit cell is effectively non-resonant. In other embodiments, the coupler is a switch configured to change from the first impedance state to the second impedance state in response to a signal from the MRI machine, to shift the resonant frequency of the unit cell away from the working frequency of the MRI machine.

In yet another embodiment, a method of magnetic resonance imaging a specimen includes providing an MRI machine having a bore and a working frequency, placing the specimen within the bore, and placing, in the bore with the specimen, an array of unit cells. The array of unit cell is sized to be disposed within a bore of the MRI machine along with a specimen in the bore, when the MRI machine is imaging the specimen. Each unit cell has a resonant frequency, and the array has a resonance frequency at or near the working frequency of the MRI machine. Then, the method includes operating the MRI machine, in ways known in the art, to image the specimen.

In a preferred embodiment, the MRI machine is a 1.5 Tesla MRI machine having a working frequency of 64 MHz, and the resonance frequency of the array is within 5 percent (+/−5%, inclusive) of 64 MHz. In another preferred embodiment, the MRI machine is a 3 Tesla MRI machine having a working frequency of 128 MHz, and the resonance frequency of the array is within 5 percent (+/−5%, inclusive) of 128 MHz.

BRIEF DESCRIPTION OF THE DRAWINGS

The foregoing features of embodiments will be more readily understood by reference to the following detailed description, taken with reference to the accompanying drawings, in which:

FIGS. 6A, 6B, 6C, 6D and 6E schematically illustrate an embodiment of, and some characteristics of, a broadside-coupled split ring resonator;

FIGS. 8A, 8B, 8C, 8D, 8E, 8F and 8G schematically illustrate embodiments of tunable unit cells;

DETAILED DESCRIPTION OF SPECIFIC EMBODIMENTS

An apparatus having a plurality of resonators increases signal-to-noise ratio of radiofrequency ("RF") signals emitted by a specimen and captured by an MRI machine, and does so without increasing the power transmitted by the MRI machine. In some embodiments, the apparatus increases the magnetic field component of radiofrequency energy during both signal transmission of radiofrequency energy from the MRI machine to the specimen, and transmission of radiofrequency signals from the specimen to the MRI machine, while in other embodiments, the apparatus increases the magnetic field component of radiofrequency energy only during transmission of radiofrequency signals from the specimen to the MRI machine, and not during transmission of radiofrequency energy from the MRI machine to the specimen. Moreover, the apparatus enhances specimen safety by substantially avoiding unwanted generation or, or increase in, an electric field. Use of the apparatus improves the images generated by the MRI machine, and/or reduces the time necessary for the MRI machine to capture the image.

Figure 1A:
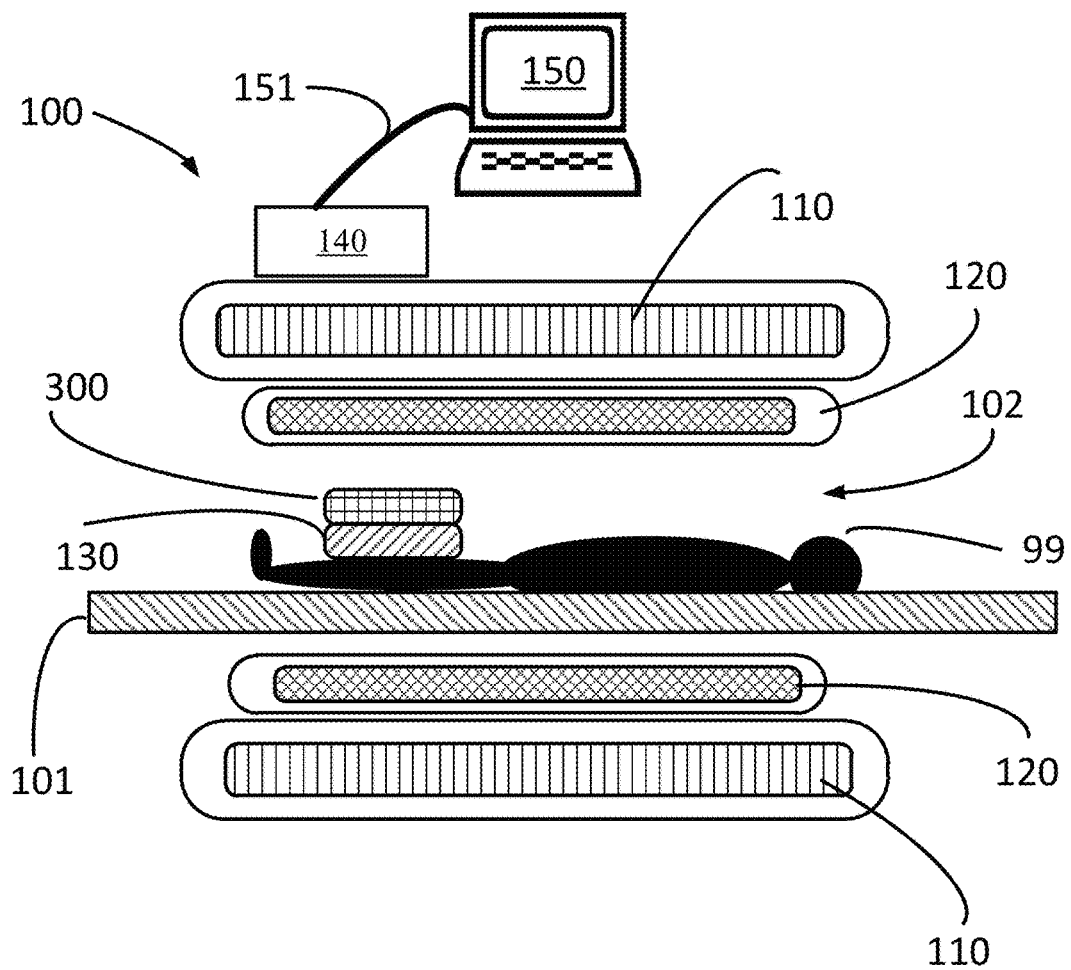
FIGS. 1A, 1B, 1C and 1D schematically illustrate an embodiment of an MRI machine.

FIG. 1A schematically illustrates an MRI machine 100 in cross-section, and shows several well-known features of such machines. A specimen 99 being scanned by the MRI machine lays on a table 101. Typically, the specimen 99 must lay as still as possible for the duration of the scan, which can be 30 minutes or more.

Main field coils 110 produce a magnetic field around and through the specimen 99, and body coils 120 subject the specimen 99 to electromagnetic (e.g., radio frequency) stimulus. In response, atoms of the specimen emit electromagnetic pulses that may be detected by body coils 120, and/or specimen coils 130. Specimen coils 130 may be preferred, because they are closer to the specimen 99, and produce signals with greater signal-to-noise ratio ("SNR") than the signals produced by the more remote body coils 120. A computer 150 is in data communication with the MRI machine, such as by communications link 151, and receives and processes the signals received by the body coils 120, and/or specimen coils 130, to produce an image of internal structures of the specimen. The body coils 120 and specimen coils 130 are wired to the MRI machine 100. The body coils are in power communication and control communication with the MRI machine to receive power and control signals required to produce the electromagnetic stimulus. Both the body coils 120 and specimen coils 130 are in data communication with the MRI machine 100 to provide to the MRI machine 100 the signals they detect from the specimen 99. To that end, some embodiments of an MRI machine include a controller 140 configured to provide control signals to the MRI machine, and/or to an array as described below in connection with control signal 821, and/or to receive signals from the body coils 120 and specimen coils 130.

The quality of the image, and the time needed for the MRI machine 100 to collect a sufficient number of emitted signals to produce the image, depend in part on the SNR of the signals received. An increase in the SNR may improve the MRI's output and/or reduce the time required to collect signals emitted by the specimen 99.

Figure 1B:
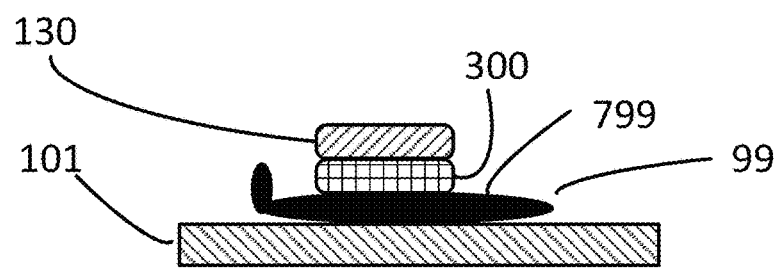

FIG. 1A and FIG. 1B each schematically illustrates an embodiment of a resonator array 300 for improving the operation of, and results produced by, an MRI machine.

In FIG. 1A, specimen coils 130 are placed between the specimen 99 and the resonator array 300, and in FIG. 1B, the resonator array 300 is disposed between the specimen 99 (in this illustration, a limb or appendage 799 of specimen 99) and the specimen coils 130. In some embodiments, the resonator array 300 may be positioned in the bore 102 of the MRI machine without specimen coils 130, for example when the MRI machine 100 uses body coils 120 to receive electromagnetic pulses emitted by the specimen 99. As used herein, the term "bore" 102 of an MRI machine 100 means the place in which the specimen 99 is disposed when being imaged by the MRI machine 100. For example, in a closed MRI machine 100, the bore 102 is the interior of the machine's toroid section; in an open MRI machine 100, the bore 102 is the space between the machine's top and bottom magnetic areas; and in an open upright MRI machine 100, the bore 102 is the space between the machines left and right magnetic areas.

Figure 1C:
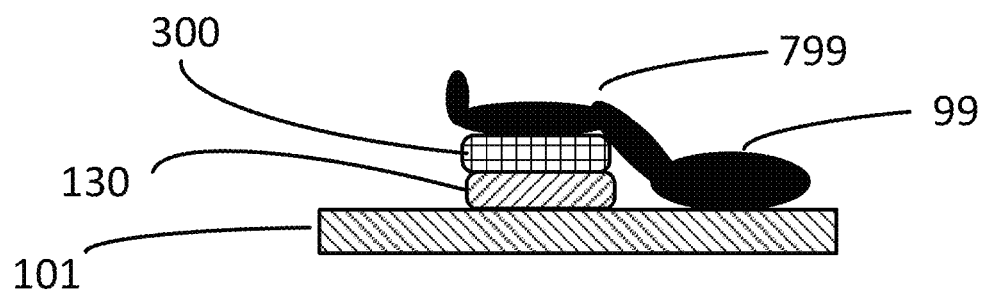
Figure 1D:
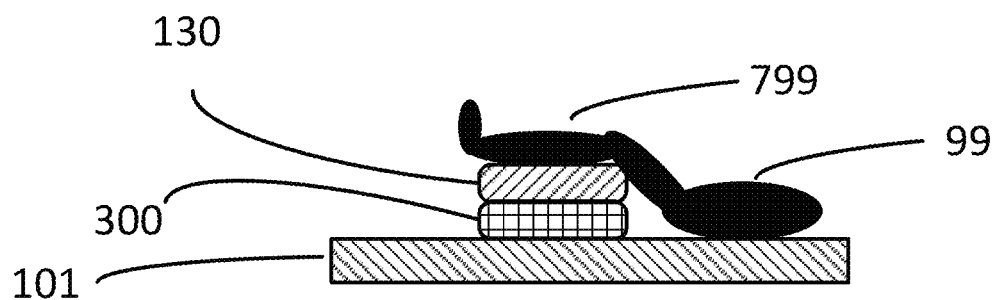

Although FIG. 1A and FIG. 1B illustrate the specimen 99 between the specimen coils 130 and resonator array 300 and the table, that is not a limitation on the use of the resonator array 300, which may be placed, with or without specimen coils 130, between the specimen 99 and the table 101, as schematically illustrated in FIG. 1C and FIG. 1D.

In contrast to the body coils 120, the resonator array 300 is passive in that it does not require or receive power signals, and in some embodiments does not require or receive control signals, in order to perform its function. In illustrative embodiments, the resonator array 300 (including its unit cells 301) is separate from, not part of, body coils 120 or specimen coils 130. Moreover, in illustrative embodiments, the resonator array 300 (including its unit cells 301) is physically separate from the MRI machine 100 and the body coils 120 and specimen coils 130, and is not wired to MRI machine 100 and the body coils 120 and specimen coils 130. Also, in contrast to both the body coils 120 and the specimen coils 130, the resonator array 300 is not in data communication with the MRI machine 100.

The inventors have discovered that use of a resonator array 300 as schematically illustrated in FIG. 1A-FIG. 1D, with or without a specimen coil 130, improves the SNR of radiofrequency signals transmitted from the MRI machine 100 to the specimen 99, and improves the SNR of signals emitted by the specimen 99 and received by the MRI machine 100, and can increase the quality of the MRI's output image, and/or reduce the time required to scan a specimen 99, each of which represents an improvement over existing MRI technologies. Due to its unusual properties, the resonator array 300, and/or its resonators 301, may be thought of as a metamaterial. However, that does not require that the resonator array 300, and/or its unit cells 301, have a negative index of refraction, negative permittivity, and/or negative permeability. In various embodiments, the resonator array 300, and/or its unit cells 301, may have a positive index of refraction, positive permittivity, and/or positive permeability.

Figure 2A:
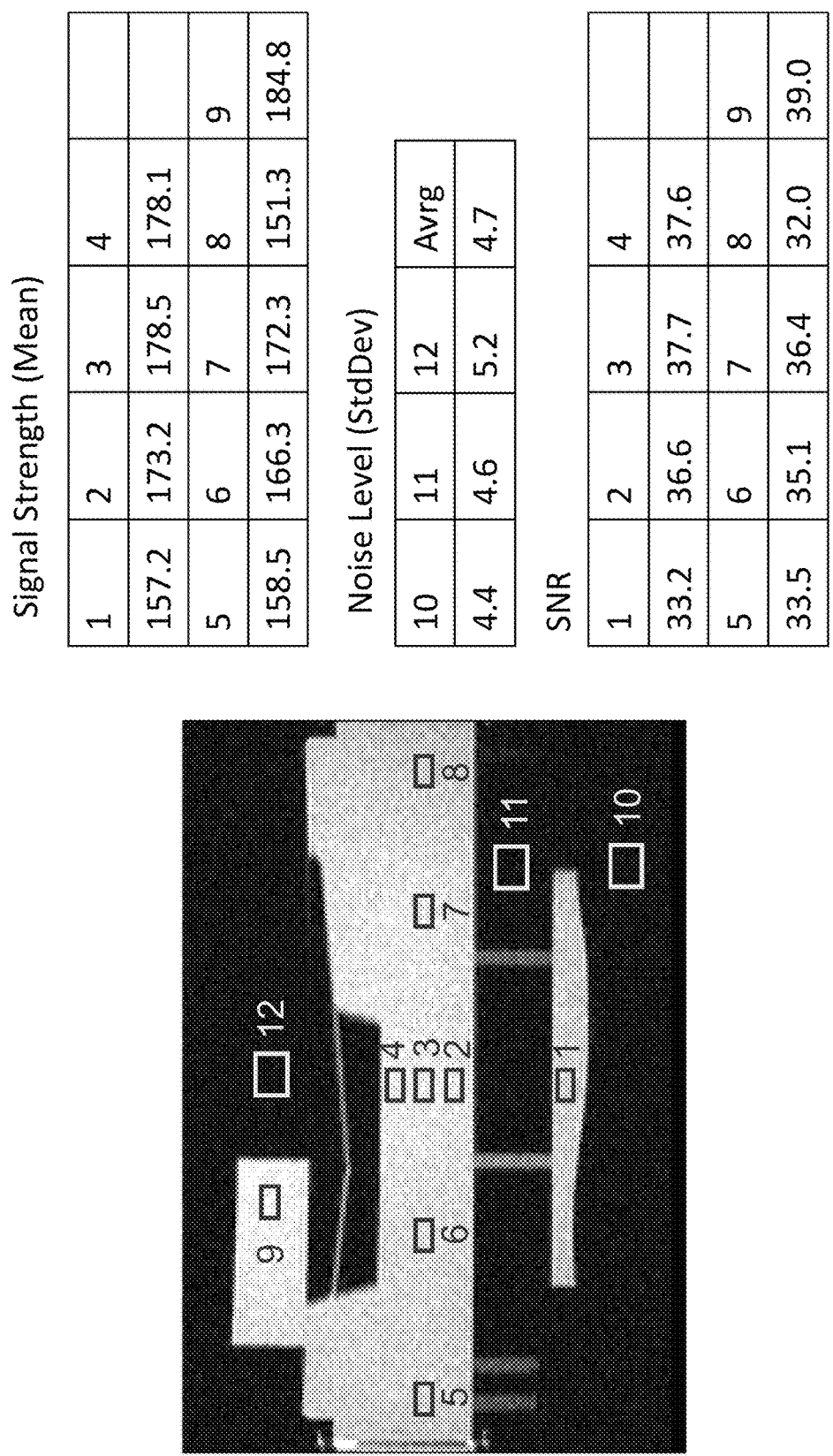
FIG. 2A is an MRI image captured without the use of a resonator array.

For example, FIG. 2A shows results of an MRI scan using conventional MRI technology without a resonator array 300. To produce these results, the inventors measured the strength of a signal at nine positions (numbered 1-9 in FIG. 2A) within the bore 102 of a 1.5 T MRI machine, and measured the noise at three positions (numbered 10-11) of the MRI machine. The inventors then calculated the average of the noise measurements, and then calculated the SNR of each signal measurement to the average of the noise measurement. The results are shown below, and reveal SNRs ranging from 33.2 to 39.0. These results may be referred-to as the "baseline" SNRs.

Signal Strength (Mean)

| 1 | 2 | 3 | 4 | |
|---|---|---|---|---|
| 157.2 | 173.2 | 178.5 | 178.1 | |
| 5 | 6 | 7 | 8 | 9 |
| 158.5 | 166.3 | 172.3 | 151.3 | 184.8 |

Noise Level (StdDev)

| 10 | 11 | 12 | Avrg |
|----|----|----|------|
| 4.4 | 4.6 | 5.2 | 4.7 |

SNR

| 1 | 2 | 3 | 4 | |
|---|---|---|---|---|
| 33.2 | 36.6 | 37.7 | 37.6 | |
| 5 | 6 | 7 | 8 | 9 |
| 33.5 | 35.1 | 36.4 | 32.0 | 39.0 |

Figure 2B:
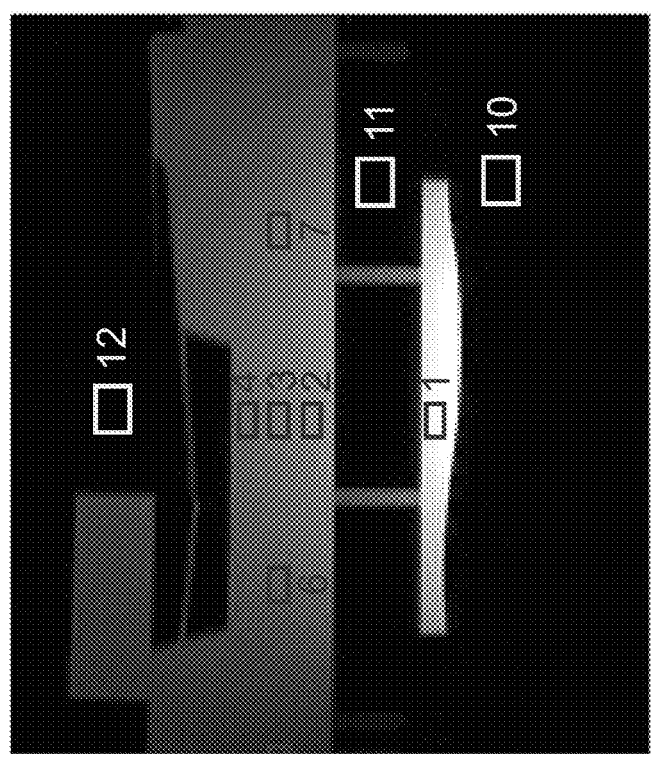
FIG. 2B is an MRI image captured with use of an embodiment of a resonator array.
Figure 2C:
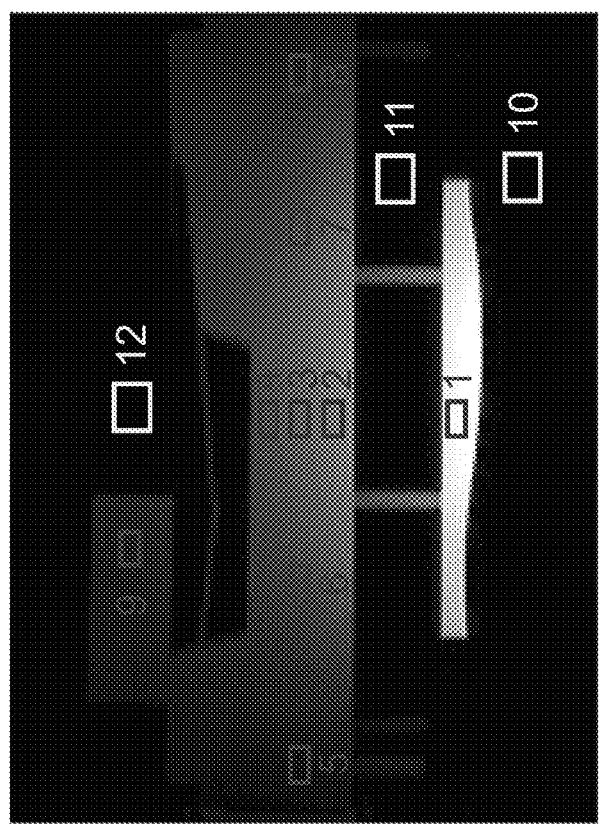
FIG. 2C is an MRI image captured with use of another embodiment of a resonator array.
Figure 5A:
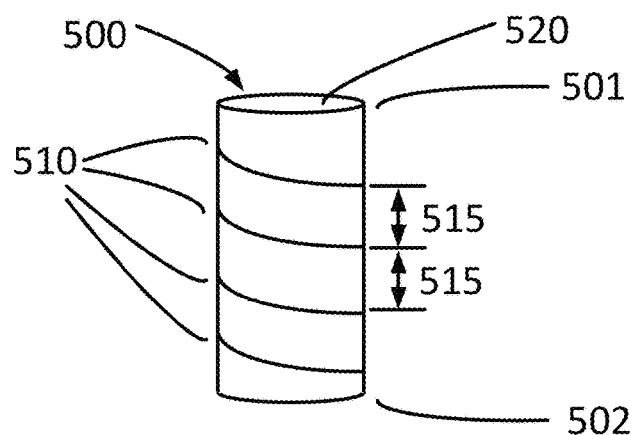
FIGS. 5A, 5B and 5C schematically illustrate an embodiment of a helical resonator.
Figure 5B:
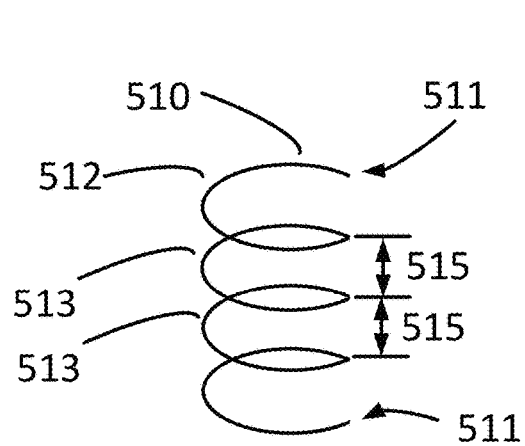
Figure 5C:
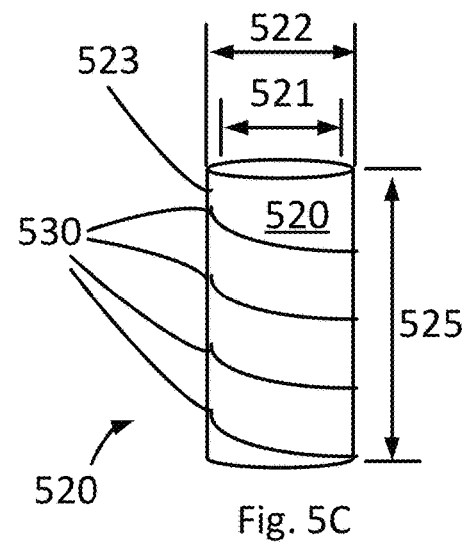

In contrast to the results shown in FIG. 2A, FIG. 2B and FIG. 2C each shows results of an MRI scan at the same nine positions using the same 1.5 T MRI machine with the resonator array 300 having unit cells 301 that are helical resonators 500 (e.g., FIG. 5A-5C). To produce these results, the inventors measured signal and noise in the way described above in connection with FIG. 2A, but obtained significantly improved SNRs.

In the embodiment for FIG. 2B, the SNRs were considerably higher than the baseline SNRs. The results are shown below, and reveal SNRs ranging from 68.4 to 277.3. Comparing the SNR for location 1 in FIG. 2B to the results for location 1 in FIG. 2A shows a large increase in SNR—from a baseline SNR of 33.2 to an improved SNR of 277.3.

Signal Strength (Mean)

| 1 | 2 | 3 | 4 | |
|---|---|---|---|---|
| 1174 | 640.4 | 546.6 | 481.1 | |
| 5 | 6 | 7 | 8 | 9 |
| 193.1 | 404.5 | 428.6 | 267.6 | 289.7 |

Noise Level (StdDev):

| 10 | 11 | 12 | Avrg |
|----|----|----|------|
| 4.1 | 4.7 | 3.9 | 4.2 |

SNR

| 1 | 2 | 3 | 4 | |
|---|---|---|---|---|
| 277.3 | 151.3 | 129.1 | 113.6 | |
| 5 | 6 | 7 | 8 | 9 |
| 45.6 | 95.5 | 101.2 | 63.2 | 68.4 |

In the embodiment for FIG. 2C employed an array 300 in which the unit cells 301 had different periodicity (i.e., different spacing relative to one another) than the array employed to generate FIG. 2B. That embodiment also produced SNRs at the same nine positions that are considerably higher than the baseline SNRs. The results are shown below, and reveal SNRs ranging from 46.2 to 401.5 Comparing the SNR for location 1 in FIG. 2C to the results for location 1 in FIG. 2A shows a large increase in SNR—from a baseline SNR of 33.2 to an improved SNR of 401.5.

Signal Strength (Mean)

| 1 | 2 | 3 | 4 | |
|---|---|---|---|---|
| 1258.0 | 605.9 | 498.2 | 381.7 | |
| 5 | 6 | 7 | 8 | 9 |
| 95.9 | 363.6 | 343.1 | 156.6 | 144.9 |

Noise Level (StdDev):

| 10 | 11 | 12 | Avrg |
|---|---|---|---|
| 2.7 | 3.5 | 3.2 | 3.1 |

SNR

| 1 | 2 | 3 | 4 | |
|---|---|---|---|---|
| 401.5 | 193.4 | 159.0 | 121.8 | |
| 5 | 6 | 7 | 8 | 9 |
| 30.6 | 116.0 | 109.5 | 50.0 | 46.2 |

In general, a resonator array 300 increases the SNR of signals emitted by a specimen. For a given MRI machine, relative to the SNR of signals received by that MRI machine without use of a resonator array, embodiments of a resonator array 300 increases the SNR of such signals to at least 45.6, 50, 60, 95, 100, 120, 150, and/or at least 193.4, or any point between 45 and 401.

Resonator Array

Figure 3A:
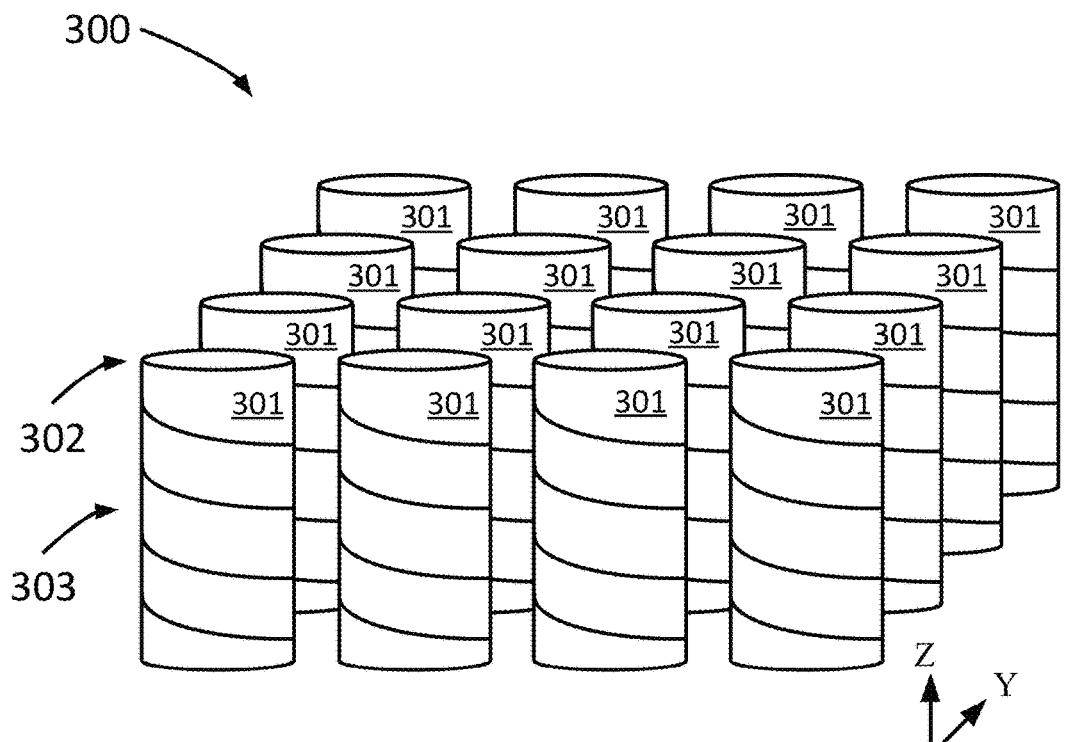
FIG. 3A and FIG. 3B schematically illustrate an embodiment of a resonator array.
Figure 3B:
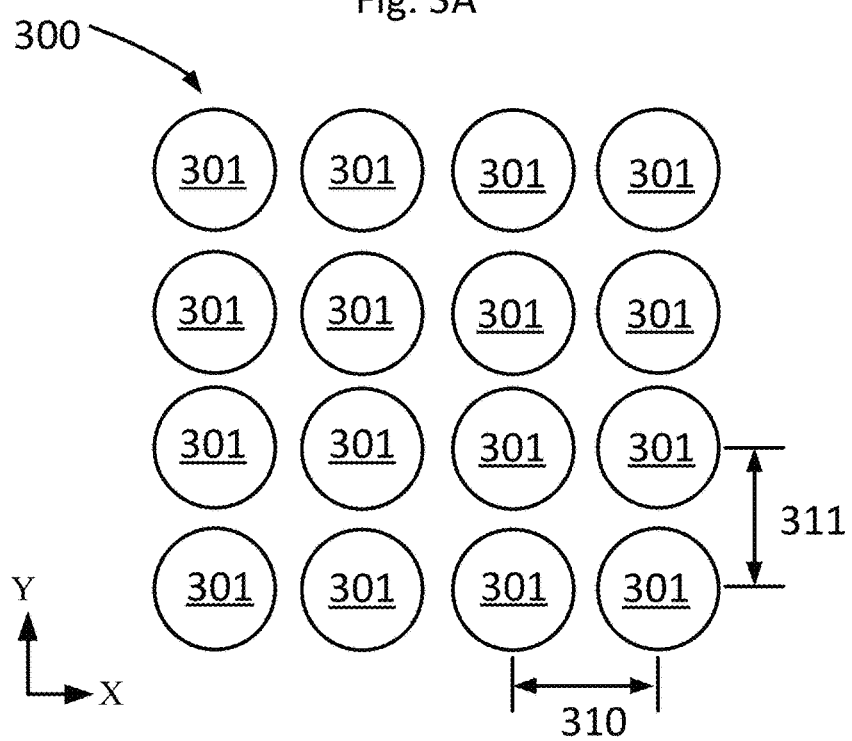
Figure 3C:
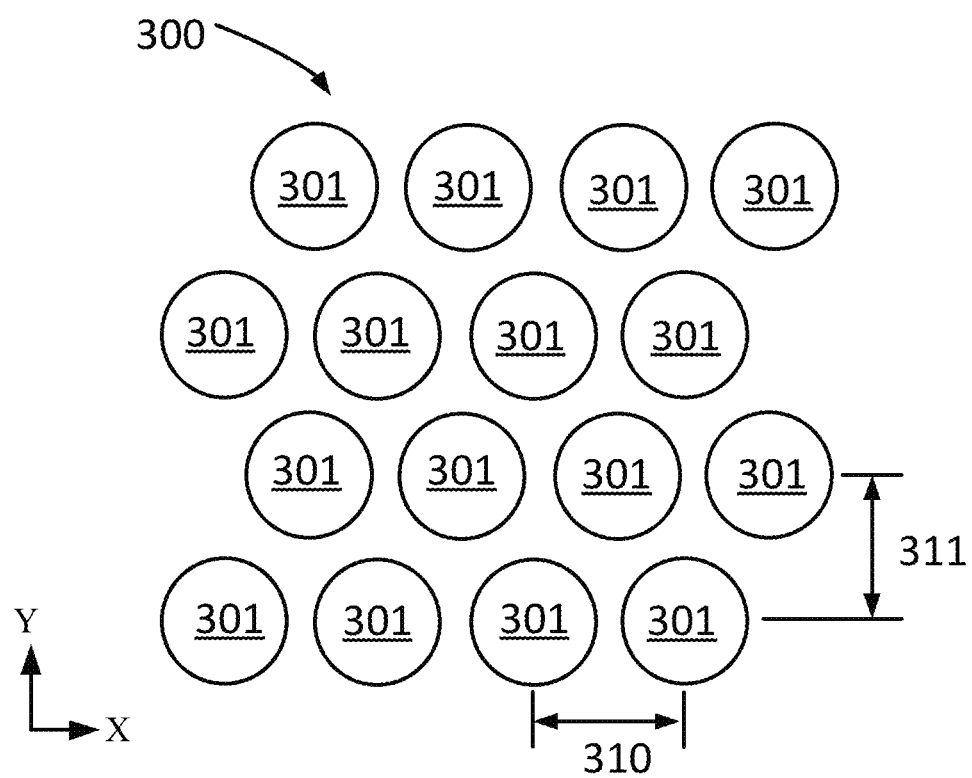
FIG. 3C schematically illustrates an embodiment of a honeycomb resonator array.

An illustrative embodiment of a resonator array 300 is schematically illustrated in FIG. 3A and FIG. 3B. The array 300 in this embodiment includes 16 unit cells 301, in a 4×4 array, but other embodiments may use more or fewer unit cells 301, and may be arranged in different arrangements, such as square, honeycomb [FIG. 3C], or rectangular for example.

Each unit cell 301 may also be referred to as a "resonator," because it is configured to resonate in response to applied electromagnetic signals, such as signals applied to a specimen 99 by an MRI machine 100, and/or signals received by the unit cell 301 from a specimen 99 in the MRI machine 100. For example, each unit cell may have an inductance (L) and a capacitance (C), and therefore resonate as do LC resonators known in the electrical engineering arts. Each unit cell 301 has a resonant frequency, and has a Q, as described in connection with FIG. 4A.

Figure 4A:
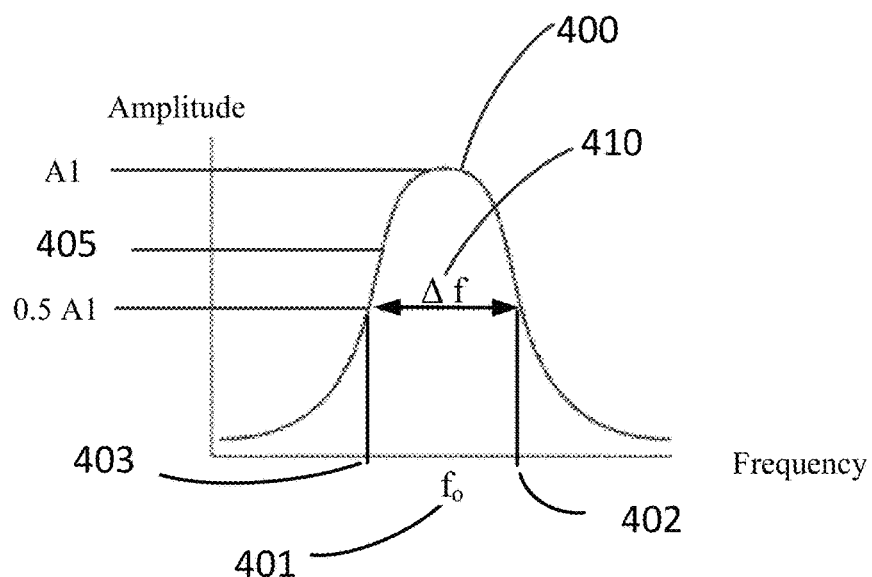
FIG. 4A is a graph illustrating quality factor of a resonating structure.

FIG. 4A graphically illustrates quality factor of a resonating device. A resonating unit cell may be characterized, in part, by its quality factor, which may be referred to as its "Q-factor," or simply as its "Q." A unit cell's Q-factor is a measure of its resonance characteristics.

For example, unit cell 301 may receive an electromagnetic signal emitted by an atom of a specimen 99 in an MRI machine 100, or from the MRI machine itself, and that electromagnetic energy may include energy at one or more frequencies. The energy will resonate in the unit cell 301, in ways known from LC circuits from the art of electrical engineering.

Ideally, the energy resonates at the resonant frequency $f_o$ (401) of the unit cell, although the unit cell 301 may resonate to some degree at lower frequencies as well, as illustrated by the curved spectrum in FIG. 4A. The maximum energy may be at frequency $f_o$ (401), which may be referred to as the center frequency, represented by amplitude A1. At other frequencies, the energy is less than that at the center frequency 401, as also schematically illustrated in FIG. 4A. At some frequency 402 above the center frequency 401 (which may be known as the upper 3 dB frequency), and at another frequency 403 below the center frequency (which may be known as the lower 3 dB frequency), the energy in the resonating signal will be half of the energy at the center frequency 401. The spectrum 400 in FIG. 4A shows that some of the energy resonating in the unit cell 301 is above a noise floor, indicated at point 405.

The Q of the unit cell 301 is then defined as the ratio of the center frequency ($f_o$) divided by difference ($\Delta f$ or delta-f) between the upper 3 dB frequency and the lower 3 dB frequency. In FIG. 4A, the Q is the center frequency 401 divided by the frequency difference 410 between upper 3 dB frequency 402 and lower 3 dB frequency 403. As such, Q is a dimensionless parameter.

In operation, a unit cell 301 may receive a packet of electromagnetic energy (e.g., RF energy) from one or more atoms in a specimen 99, the electromagnetic energy having a frequency at or near the working frequency of the MRI machine. For example, in preferred embodiments the electromagnetic energy having a frequency within +/−5% (inclusive) of the working frequency of the MRI machine is defined as being at or near the working frequency of the MRI machine. Over time (e.g., during the operation of the MRI machine), each unit cell 301 will receive many packets of electromagnetic energy, and store the sum of that energy. The higher the Q of the unit cell 301, the more efficiently the unit cell 301 stores the energy it receives.

In addition, as the unit cell 301 resonates, it amplifies the magnetic field component of that received electromagnetic energy, and increases the signal-to-noise ratio of the received electromagnetic energy. As such, each unit cell 301, individually, has the ability to resonate, without regard to other unit cells (if any) that may be nearby, and has some ability to amplify the magnetic field component of received electromagnetic energy.

The inventors have discovered, however, some limitations on the usefulness of individual unit cells 301. First, a single unit cell 301 has limited capacity to amplify the magnetic field component of received electromagnetic energy. Second, a unit cell 301 may have a resonant frequency that is not well matched to the MRI machine 100, in which case its ability to amplify the magnetic field component of received electromagnetic energy is less efficient than it would otherwise be. Third, it is not possible to change the resonant frequency, and/or the Q, of an individual unit cell 301, at least without disassembling and rebuilding the unit cell 301.

The inventors have also discovered, however, that an array 300 of unit cells 301 has characteristics that are different from a mere aggregation of the characteristics of its constituent unit cells 301. In other words, the resonator array 300 exhibits a synergy.

Figure 5D:
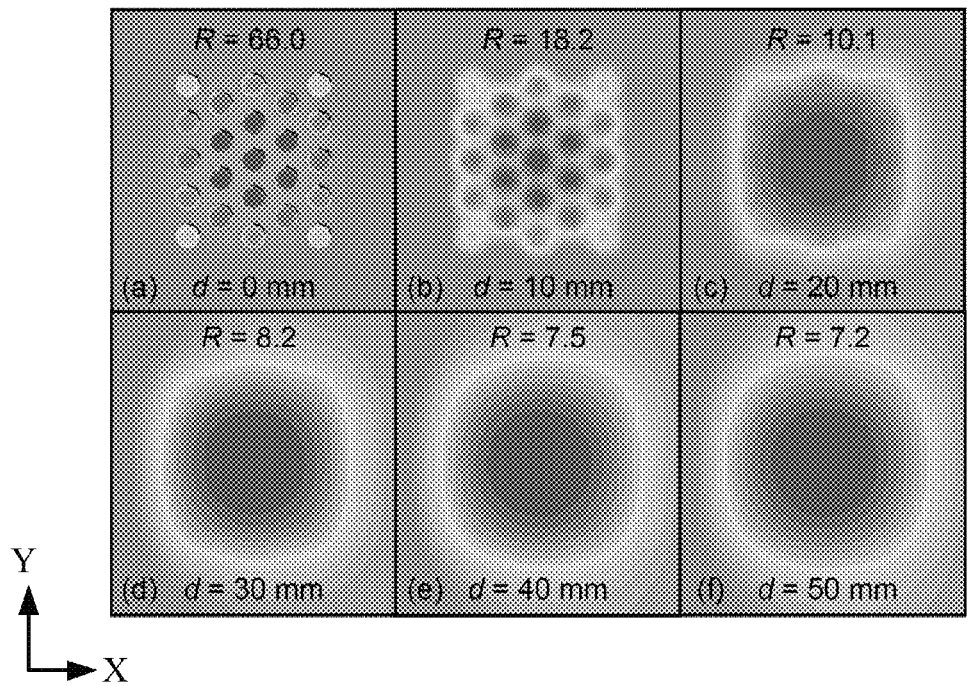
FIG. 5D and FIG. 5E schematically illustrate operating characteristics of an embodiment of an array of helical resonators.

For example, an array 300 of unit cells provides a homogenous amplification of the magnetic field component of received electromagnetic energy (see, e.g., FIG. 5D and the text that describes that figure).

In addition, the resonant frequency of the array 300 may not be the same as the resonant frequencies, respectively, of its constituent unit cells 301. Rather, the unit cells 301 couple to one another to produce the resonant frequency of the array 300. To that end, in preferred embodiments, the unit cells 301 magnetically couple to one another, and are not wired to one another.

Moreover, the resonant frequency of the array 300 may be tuned by adapting the spacing of the unit cells 301 within the array 300.

In addition, the array 300 is modular, in that unit cells 301 may be added to an array 300 at the same periodicity (i.e., X-pitch 310 and/or Y-Pitch 311) of unit cells 301 already in the array 300, without significantly changing the resonance characteristics of the array 300. Adding unit cells 301 to an array 300 at the same periodicity of unit cells 301 already in the array 300 does not change the resonance characteristics of the array as much as changing the periodicity of the unit cells 301 of the array 300. Adding unit cells in this way may be desirable, for example, to increase the size of the array 300 to image a larger specimen 99, or a larger portion of a specimen 99.

Similarly, unit cells 301 already in an array 300 with a given periodicity may be removed from the array 300 without significantly changing the resonance characteristics of the array 300. Removing unit cells 301 from an array 300 with a given periodicity does not change the resonance characteristics of the array as much as changing the periodicity of the unit cells 301 of the array 300. Removing unit cells may be desirable, for example, to reduce the size of the array to fit into the bore 102 of an MRI machine 100, or to image a smaller specimen 99, or a smaller portion of a specimen 99.

The resonator array 300 is configured to have a resonance frequency at or near the working frequency of the MRI machine 100 (i.e., the resonance frequency of the array is within +/−5%, inclusive, of the working frequency of the MRI machine 100). For example, the working frequency (or "operating frequency") of a 1.5 Tesla (i.e., 1.5 T) MRI machine is approximately 64 MHz (which is a radiofrequency for purposes of this disclosure), and the working frequency of a 3 Tesla (i.e., 3 T) MRI machine is approximately 128 MHz (which is also a radiofrequency for purposes of this disclosure).

The resonance frequency of the resonator array 300 is partially determined by the periodicity (spacing) of the unit cells 301 of the array 300, and also by the resonance frequency of the individual unit cells 301. In the illustrative resonator array 300 of FIG. 3A and FIG. 3B, the resonators are evenly spaced: each unit cell 301 is separated by a dimension, the X-pitch 310, of 37.33 mm in the X-axis, and by a dimension, the Y-pitch 311, of 37.33 mm in the Y-axis. In this configuration, the resonance frequency 463 of the resonator array 300 is centered at the working frequency 452 of the MRI machine 100. In general, the difference between the working frequency 452 of the MRI machine and the resonance frequency of the resonator array 300 may be specified by the designer or operator of the MRI machine. In preferred embodiments, the resonance frequency of the resonator array 300 is within +/−5% (inclusive) of the working frequency 452 of the MRI machine.

Figure 4B:
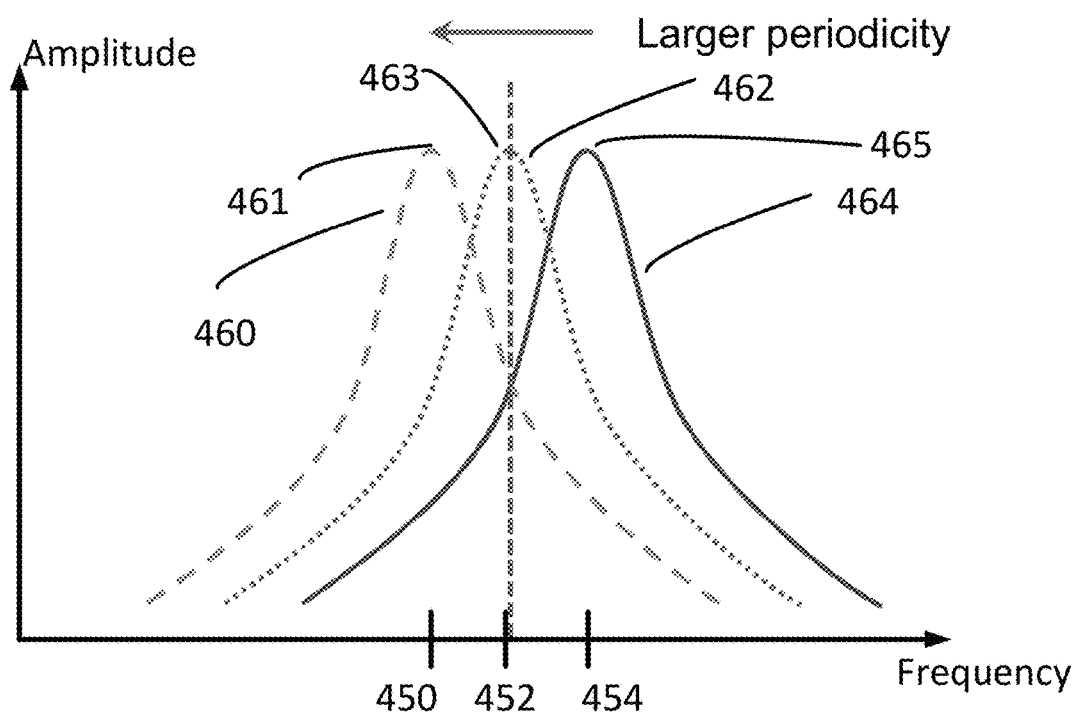
FIG. 4B graphically illustrates the relationship between the periodicity of a resonator array and its frequency response relative to the working frequency of an MRI machine.

At a larger periodicity (i.e., greater X-pitch 310 and Y-pitch 311), the resonance frequency of the resonator array 300 is reduced, and at a lower periodicity (i.e., smaller X-pitch 310 and Y-pitch 311), the resonance frequency of the resonator array 300 is increased. FIG. 4B graphically illustrates the relationship between the periodicity of a resonator array 300 and its frequency response relative to the working frequency 452 of an MRI machine. Curve 462 schematically illustrates the resonance of an array 300 tuned to the working frequency 452 of the MRI machine 100, with a resonant frequency at point 463. In contrast, curve 460 schematically illustrates the resonance of the array 300 tuned to a frequency 450 slightly below the working frequency 452 of the MRI machine 100, with its resonant frequency at point 461, and curve 464 schematically illustrates the resonance of the array 300 tuned to a frequency 454 slightly higher than the working frequency 452 of the MRI machine, with its resonant frequency at point 465.

Consequently, the resonance frequency of the resonator array 300 can be adjusted and established as necessary or desired for a given MRI machine or application. For example, the inventors have realized that the presence of soft tissue near the array 300 may change the permittivity of the area surrounding the array 300. If such a change of permittivity interferes with or degrades the operation of the MRI machine 100 or resonator the resonance frequency of the resonator array 300 may be adjusted by changing the spacing of the unit cells 301 of the resonator array 300.

Helical Unit Cell

An illustrative embodiment 500 of a unit cell 301 in the form of a helical resonator 500 is schematically illustrated in FIG. 5A, and FIG. 5B, and FIG. 5C. The resonator 500 includes a helical conductor 510 around a low-dielectric core 520.

The helical conductor 510, which may be copper, is wrapped around the core 520 so that each successive turn (513) (or "loop") around the core is separated from its predecessor by a gap 515.

The unit cell 301 has both inductance (L) and capacitance (C). The inductance arises from the coiled conductor 510, and the capacitance arises in the gap 515 between successive turns 513 of the conductor 510. Consequently, the resonant frequency of the unit cell 301 is determined, at least in part, by the number of turns 513 of the conductor 510 and the dimensions of the gap 515 between turns 513. A designer may therefore establish the resonant characteristics of the unit cell 301 to suit a desired application by establishing the inductance and capacitance through specification of its properties (e.g., the number of turns 513 and/or the gap 515) of the coiled conductor 510 and/or the dielectric constant (k) and/or loss angle of the core 520. Moreover, the resonant frequency of an array 300 of unit cells 301 may be tuned by specifying, or adapting, the resonant characteristics of the unit cells 301 by, for example, increasing or decreasing the number of turns 513 of the conductor 510, and/or increasing or decreasing the gap 515 between turns 513 of the conductor 510.

In some embodiments, the conductor 510 does not overlap itself, but in other embodiments the conductor 510 may overlap itself as long as there is no direct electrical contact between different regions of the conductor 510. For example, the conductor 510 may overlap itself if it includes an electrically insulating coating 512.

FIG. 5C schematically illustrates a core 520 without the conductor 510. In some embodiments, the outer surface 523 of the core 520 includes a helical groove 530 to receive the conductor 510 and define its helical shape.

The ends 511 of the conductor 510 do not connect to one another, or to another conductor, or to the conductor 510 of another resonator. Consequently, the conductor 510 may be referred to as an open-loop resonator or an open-loop coil or an open-loop helical resonator.

In preferred embodiments, the core 520 has a low dielectric constant (k) and a low loss angle. For example, the core 520 may be made of materials such as polyvinylchloride ("PVC"), which as a dielectric constant of 3 (k=3). As used herein, a dielectric constant (relative permittivity) lower than 15 is considered a "low-dielectric constant" (or "low relative permittivity") and dielectric constant (relative permittivity) greater than or equal to 15 is considered a "high-dielectric constant" (or "high relative permittivity").

Figure 5E:
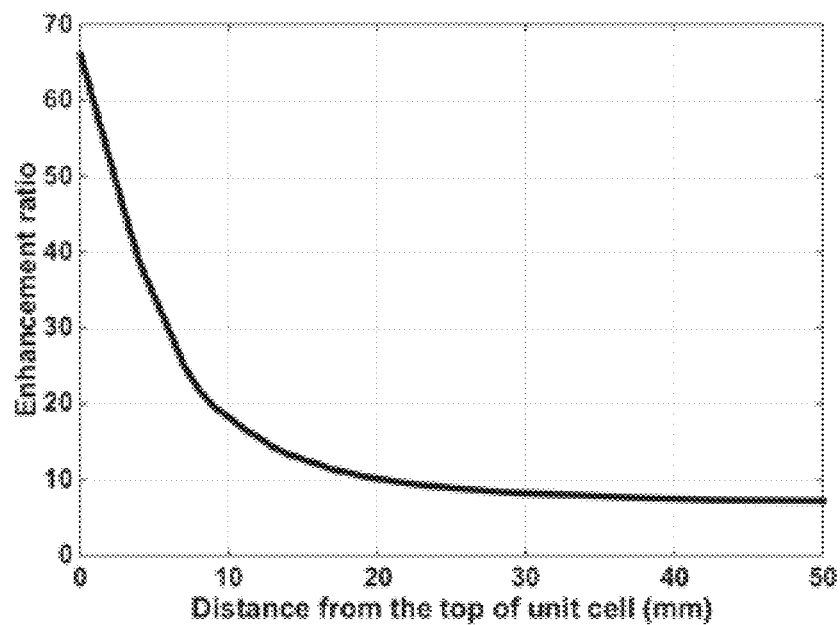

The core 520 in some embodiments may, however, have a dielectric constant of greater than 3, which reduces the size of the unit cell 301 while, possibly with adjustments of other properties of the unit cell 301, maintaining the same resonant characteristics. For example, the inventors experimented with water, which has a permittivity of approximately 80 at 20 degrees Celsius, as schematically illustrated in FIG. 5G and FIG. 5H and FIG. 5I. Unit cell 500 is placed in a dish 560 encircled by a coupling loop 561 which is coupled to a network analyzer. When the dish 560 is filled only with air, the unit cell 500 has a resonant frequency of 63 MHz, as shown by point 567 in FIG. 5I. However, when the dish contains water such that water fills about ten percent (10%) of the core 520 (the surface 566 of the water at 10%), the unit cell 500 has a resonant frequency of 55 MHz, as shown by point 568 in FIG. 5I. When the dish contains water such that water fills about twenty percent (20%) of the core 520 (the surface 566 of the water at 20%), the unit cell 500 has a resonant frequency of 39 MHz, as shown by point 569 in FIG. 5I. Consequently, it can be understood that including within a given unit cell 500 a material with a permittivity higher than the permittivity of air, the resonant frequency of the unit coil 500 is reduced. Conversely, to a produce a unit cell 500 having a given resonant frequency, the unit cell 500 can be made smaller (e.g., have fewer turns 513), relative to a unit cell 500 having air in its core 520, of the interior 503 of the unit cell 500 has a relatively higher relative permittivity, for example between 86 and 173. For example, some embodiments include a core with a permittivity of between 86 and 173. In some embodiments, the relative permittivity may be even greater than 173. In some such embodiments include a core 520 made of titanium dioxide.

Some embodiments omit the core 520, and include a conductor 510 fixed into a helical shape (see, for example, FIG. 5B). In such embodiments, in air, the volume within the helical coil 510 has a dielectric constant of air, which is near one (k=1).

The characteristics of a helical resonator 500 may be determined by the type of MRI machine in which they will be used. In the embodiment of FIG. 5A, the core 520 is a hollow cylinder with an outside diameter 522, and an inside diameter 521, and a height 525. That shape and those dimensions, however, are not limitations of all embodiments, and other solid or hollow shapes may be used, including shapes having cross-sections that are square or triangular, to name but a few examples. Characteristics of illustrative embodiments of helical resonators 500 are given below for 1.5 T MRI machines and 3 T MRI machines.

| Characteristic | 1.5T | 3T |
| --- | --- | --- |
| Outside diameter 522 | 3.0 cm | 2.0 cm |
| Height 525 | 3.2 cm | 3.0 cm |
| Number of turns of conductor 510 | 25 | 25 |
| X-pitch 310 | 3.7 cm | 2.3 cm |
| Y-pitch 311 | 3.7 cm | 2.3 cm |

Operation of Resonator Array

In operation, the resonator array 300 is placed on or near a specimen 99 in an MRI machine 100, as schematically illustrated for example in FIG. 1A, FIG. 1B, FIG. 1C and FIG. 1D.

The resonator array 300 resonates at or near the working frequency 452 of the MRI machine 100, and thereby increases the magnetic field strength of the RF signals emitted by the specimen 99. In this way, the SNR of the RF signals is increased.

The resonator array 300 increases the magnetic field component of radiofrequency energy during signal transmission by the MRI machine 100 to the specimen 99, and reception of radiofrequency energy from the specimen 99 to the MRI machine.

For example, FIG. 5D graphically illustrates the magnetic field intensity at various elevations, above the top 302 of the unit cells 301 (e.g., in the Z axis), within an embodiment of a resonator array 300 in which the unit cells 301 are helical resonators 500. FIG. 5E graphically illustrates the magnetic field enhancement ratio at the center point of said array 300 as a function of distance from the middle 303 of the unit cells 301, and shows that the enhancement is greatest near the middle 303 of the unit cells 301, and decreases with distance from the middle 303 of the unit cells. It should be noted, from FIG. 5D, that the magnetic field enhancement is substantially uniform across the resonator array 300. In the helical resonator 500, magnetic field enhancement arises due to the overlap between the self-resonant frequency of the helical resonator 500 and the frequency of excitation of the magnetic field.

Beneficially, the resonator array 300 also substantially avoids generation of an electric field, or minimizes an increase in the electrical field component of those RF signals. For example, an electric field created at one end 501 of a resonator 500 very nearly completely cancels an electric field at the other end 502. Also, in various embodiments increase in the electrical field component of those RF signals less than the increase the magnetic field component of those RF signals. This is beneficial for specimen safety, since electrical fields may cause burns to the specimen, for example. Specifically, the helical resonators 500 are configured such that they do not couple with the electric field of the RF signals, thereby mitigating amplification by the helical resonators 500, and the array 300, of the electric field component of RF signals.

Figure 5F:
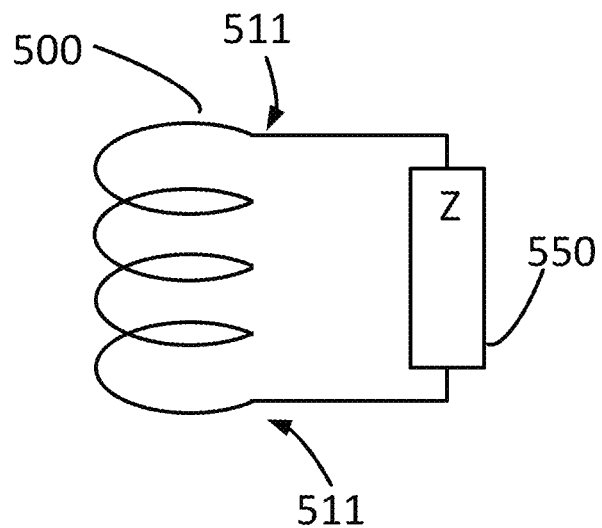
FIG. 5F schematically illustrates a helical resonator cell having an additional impedance.
Figure 5G:
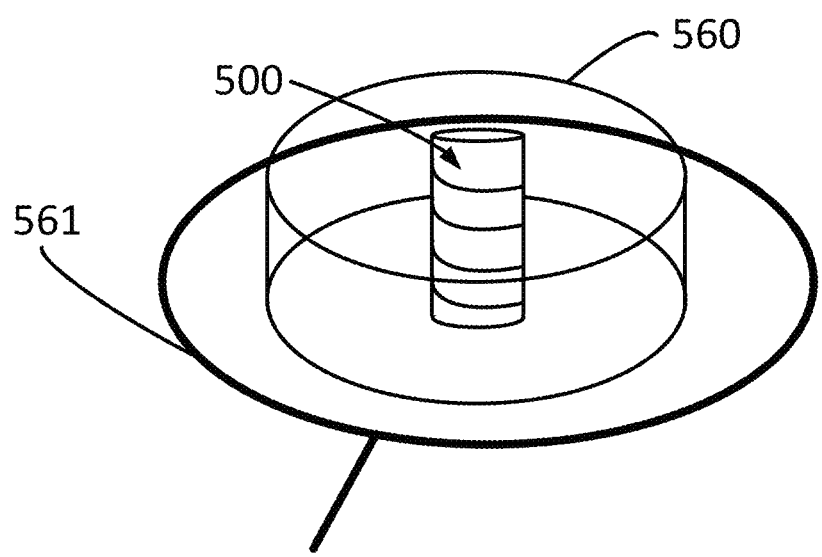
FIG. 5G and FIG. 5H schematically illustrate an embodiment of a unit cell with water in a dish to demonstrate the relationship between the unit cell's resonant frequency and the permittivity of the volume of the interior of the unit cell.
Figure 5H:
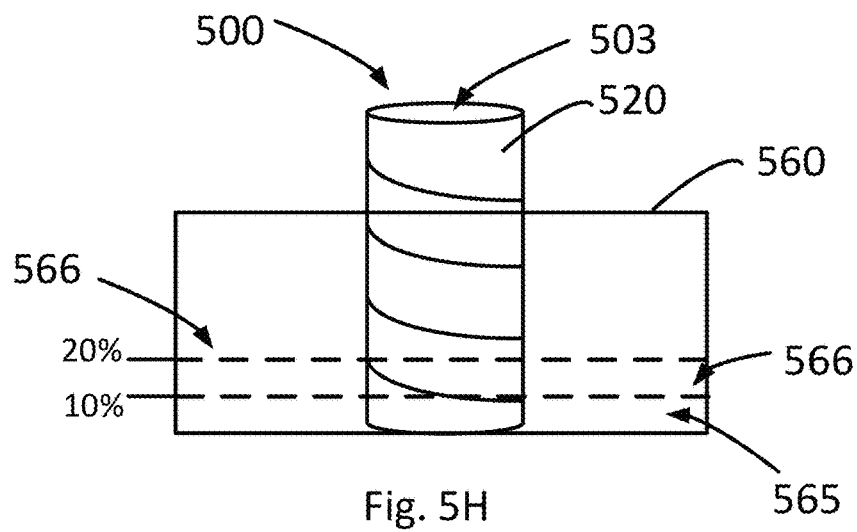
Figure 5I:
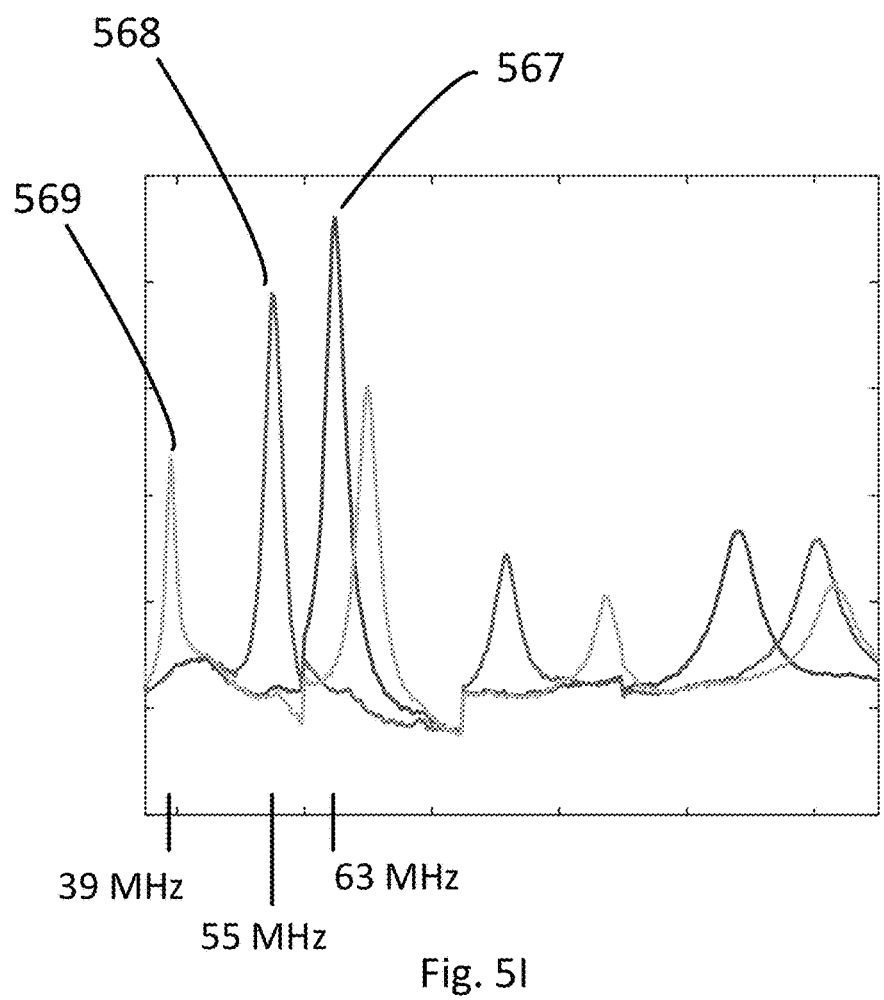
FIG. 5I schematically illustrates the relationship between the unit cell's resonant frequency and the permittivity of the volume of the interior of the unit cell.

FIG. 5F schematically illustrates an alternate embodiment of a helical resonator 500, including an additional fixed reactance 550 electrically coupled between the ends 511 of the unit cell's conductor 510. The additional reactance 550 is in addition to the inductance and/or capacitance of the conductor 510. The additional reactance 550 may be a capacitance (C), or an inductance (L). In practice, the additional reactance 550 interacts with the capacitance or inductance of the other structures of the helical resonator 500. For example, because the resonant frequency of the helical resonator 500 is dominated by $1/\sqrt{LC}$, inclusion of an inductor (L) in the additional reactance 550 produces a helical conductor 500 with the same resonant characteristics described above, but with a fewer number of turns 513 or/and a smaller diameter 521 of the helix. Likewise, inclusion of a capacitor (C) in the additional reactance 550 produces a helical conductor 500 with the same resonant characteristics described above, but requires less capacitance from the helical conductor 510.

BC-SRR Unit Cell

An embodiment of a unit cell 301, in the form of a broadside-coupled split ring resonator 600 ("BC-SRR"), is schematically illustrated in FIG. 6A. The BC-SRR resonator 600 includes two "C" shaped split-ring resonators 610, 620, each defining a gap 611 and 621, respectively. The split-ring resonators 610, 620 are disposed parallel to one another in the X-Y plane of FIG. 6A, and do not intersect or physically contact one another. As illustrated in FIG. 6A, the split-ring resonators 610, 620 are positioned such that their gaps, 611 and 621, are diametrically opposed to one another (i.e., 180 degrees from one another). The BC-SRR unit cells resonate well even if the gaps 611 and 621 are not 180 degrees from one another, but this is the preferred arrangement because the inventors have discovered that this arrangement produces the lowest electrical field. The top split-ring resonator 610 defines a top surface 601 of the BC-SRR 600, and a bottom surface 602 of the BC-SRR 600, for reference.

In the BC-SRR unit cell 600, magnetic field enhancement arises due to the overlap between the self-resonant frequency of the unit cells 600 and the frequency of excitation of the magnetic field. The BC-SRR unit cells are configured so that excited electric dipoles exhibit cancellation, thereby mitigating amplification by the unit cells 301, and the array 300, of the electric field component of RF signals.

FIGS. 6B-6D schematically illustrate operating characteristics of a BC-SRR 600 configured for resonance at 64 Mhz.

FIG. 6B schematically illustrates the magnetic field (Bz) distribution in a cross-section in the X-Z plane, of a single unit cell BC-SRR 600, and FIG. 6C schematically illustrates that magnetic field distribution in the X-Y plane 10 millimeters away from the top surface 601 of the BC-SRR 600. FIG. 6D schematically illustrates the magnetic field enhancement factor at a point 10 millimeters away from the top surface 601 of the BC-SRR 600. In this embodiment, an electric field created at one end of the BC-SRR 600 (i.e., the end nearest the top surface 601) very nearly completely cancels an electric field at the other end (i.e., the end nearest the bottom surface 602).

FIG. 6E schematically illustrates an array 300 of BC-SRR unit cells 600. In this embodiment, the BC-SRRs are photo-lithographically fabricated on a high-permittivity substrate 650.

Figures 7A, 7B:
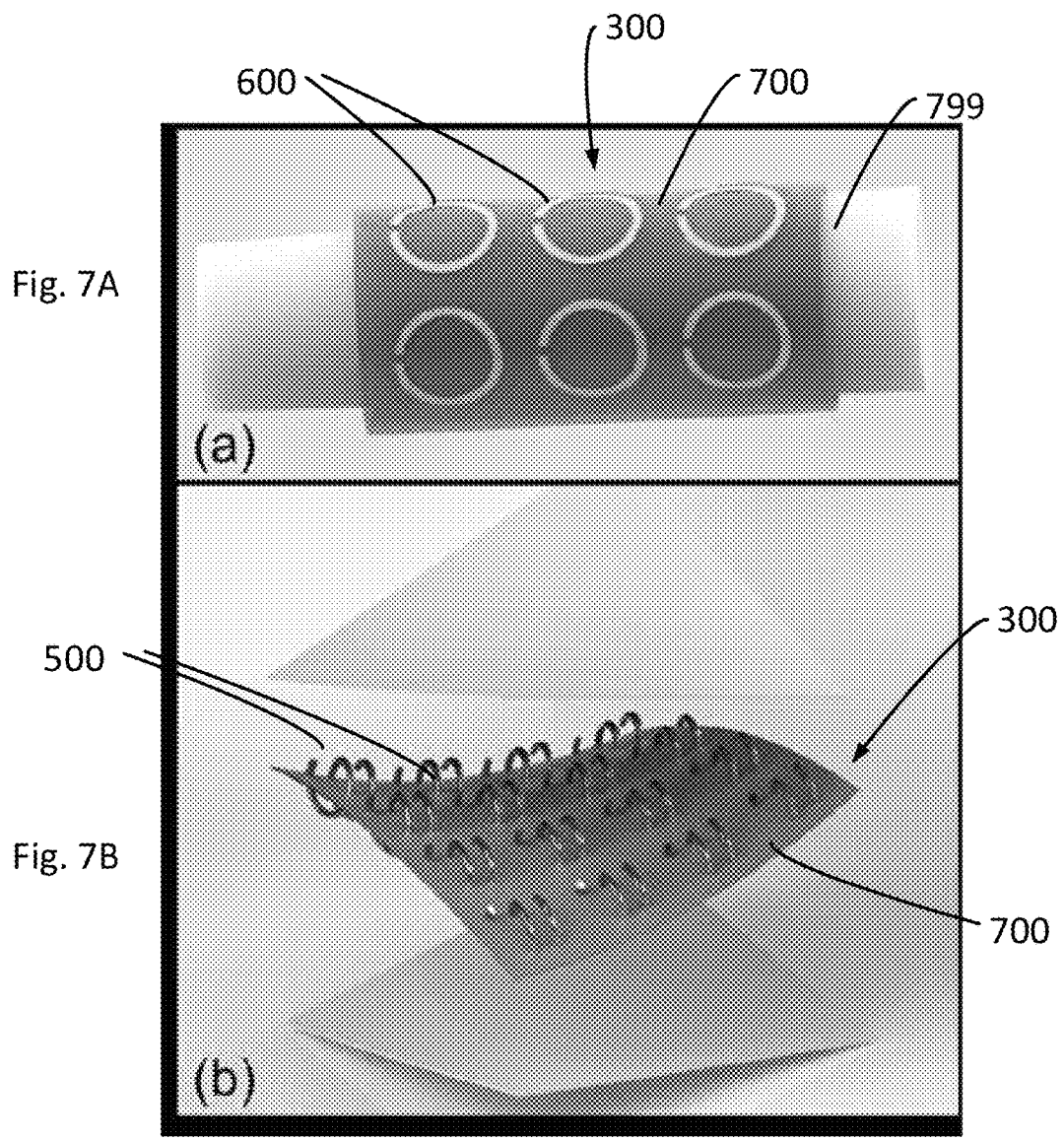
FIG. 7A and FIG. 7B schematically illustrate embodiments of flexible resonator arrays.

Embodiments of resonator arrays 300 may be rigid or flexible. For example, the array 300 of BC-SRR resonators in FIG. 6E may be rigid, while the arrays 300 of FIG. 7A and FIG. 7B are flexible. The BC-SRR array 300 of FIG. 7A has a flexible substrate 700, and as shown in FIG. 7A may even be wrapped around the limb 799 of a specimen 99, for example. Similarly, the array 300 of helical resonators 500 has a flexible substrate 700, and may be contoured to a portion of the body of a specimen 99, or even formed into a cone.

In some applications, it may be desirable to increase the magnetic field component of radiofrequency energy only during transmission of radiofrequency signals from the specimen to the MRI machine, and not during transmission of radiofrequency energy from the MRI machine 100 to the specimen 99. To that end, some embodiments include a tunable array 300 and tunable unit cells 301.

FIGS. 8A-8G schematically illustrate embodiments of tunable unit cells 301. An array 300 with tunable unit cells 301 is tunable by tuning its constituent unit cells 301.

Figure 8A:
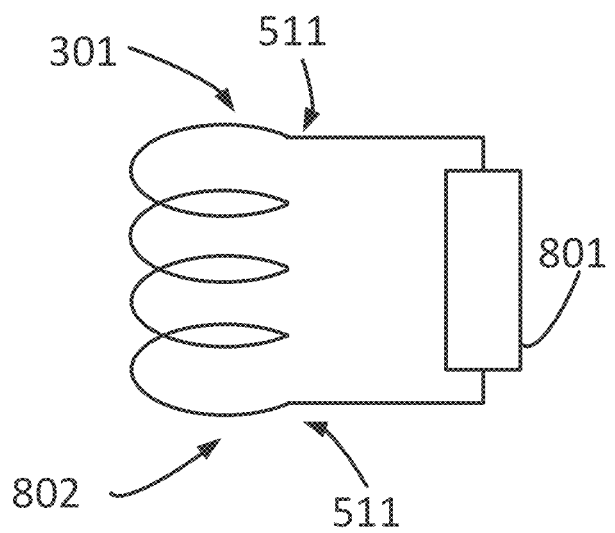

FIG. 8A schematically illustrates a tunable unit cell 301. The tunable unit cell 301 may include, for example, a helical coil 500 as described above, or a BC-SRR 600 as described above, along with a coupler 801.

The coupler 801 has at least two electrical states (or "impedance" states), including a first state in which the electrical conductivity of the coupler 801 is lower than its electrical conductivity in the second state. Stated alternately, the electrical impedance of the coupler 801 is higher in the first state than it is in the second state. The resonant properties of the unit cell 301 vary depending on the state of the coupler 801.

In the embodiment of FIG. 8A, the coupler 801 is electrically coupled between the two ends 511 of a helical coil (e.g., 500), but may be coupled to one or more unit cells in several ways, as described below. In its first state, the impedance of the coupler 801 is sufficiently high that the operation of the unit cell 301 is as described above. In the second state, however, the impedance of the coupler is lower, creating an electrical connection via a conductive path between the two ends 511 of the coil 500. That electrical connection changes the properties of the helical coil 500 so that it no longer resonates, or so that its resonant frequency is shifted to a frequency away from the working frequency 452 of the MRI machine. In general, the difference between the working frequency 452 of the MRI machine and the helical coil's resonant frequency, when the coupler 801 is in the second state, may be specified by the designer or operator of the MRI machine. For example, in preferred embodiments, when the coupler 801 is in the second state, the resonant frequency of the helical coil 500 changes such that—if it resonates at all—its resonant frequency is at least +/−15 percent different than the working frequency 452 of the MRI machine, and/or at least +/−15 percent different than its resonant frequency when the coupler 801 is in the first state. Consequently, changing the state of the coupler 801 changes the resonant properties of the unit cell 301. In general, when the resonant frequency of a unit cell 300 (in this example, the helical coil 500) is at least +/−15 percent different than the working frequency 452 of the MRI machine, and/or at least +/−15 percent different than its resonant frequency when the coupler 801 is in the first state, the unit cell is said to be "effectively non-resonant."

Moreover, in an array 300 of such unit cells 301, changing the state of the coupler 801 changes the operating properties of the array 300. For example, when the coupler 801 is in the first state, each unit cell 301, and an array 300 of such unit cells 301, operate as described above in connection with FIGS. 3A-3C, 4A-4B, 5A-5F and 6A-6E. When the coupler 801 is in the second state, the resonant properties of the array 300 are changed such that amplification of the magnetic field produced by the array 300 is reduced. In effect, each unit cell 301, and the array 300, and can be "turned on" by placing the coupler 801 in the first state, and "turned off" by placing the coupler 801 in the second state. A variety of couplers 801, unit cell 301 configurations, and array 300 configurations, are described below. In general, the coupler 801 may be referred to as a non-linear material or non-linear device.

Figure 8B:
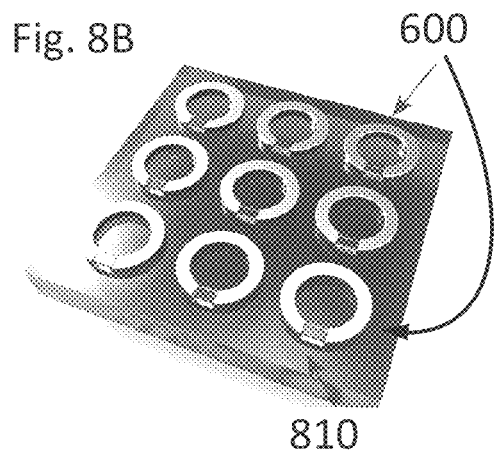

FIG. 8B schematically illustrates an array 300 of BC-SRRs 600. Each BC-SRR unit cell includes at least one coupler 801, and in some embodiments more than one coupler 801. The coupler 801 in FIG. 8B is referred to as a semiconductor patch 810. The semiconductor patch 810 may be, for example, doped silicon that changes its impedance in response to RF energy from the MRI machine 100, but not in response to the generally much lower amount of RF energy of signals from the specimen 99. The semiconductor patch may be said to be nonlinear.

In illustrative embodiments, the semiconductor material of the semiconductor patch 810 may be GaAs, InAs, or InSb, to name but a few examples. A preferred embodiment uses GaAs as the semiconductor material. Intrinsic GaAs, without doping, has a carrier density of $2.1*10^6$ $cm^{-3}$.

The properties of the semiconductor are tuned by doping. Doping is known in the semiconductor arts. In illustrative embodiments, the GaAs is doped it to have a carrier density of $3*10^7$ cm$^{-3}$.

In illustrative embodiments, a semiconductor patch 810 may be prepared from a 2 inch or 4 inch wafer (0.5 mm thick) of doped semiconductor (e.g., GaAs doped as above). The wafer is diced into patches with 3 mm by 5 mm in size, and two electrodes are patterned onto the patch in ways known in the semiconductor art, with micrometer size gap such as $2*10^{-6}$ m.

As schematically illustrated in FIG. 8A, the semiconductor patch 810 is electrically coupled (e.g., soldered) to unit cell 301. By applying alternating magnetic field (e.g., a radiofrequency electromagnetic signal), a strong electric field can be induced at the micrometer size gap as high as 400 kV/cm to excite the impact ionization at the gap.

In illustrative embodiments, when the MRI machine 100 is not applying such an alternating magnetic field (e.g., a radiofrequency electromagnetic signal), the conductivity of the semiconductor patch 810 is approximately $1*10^{-7}$ (ohm cm)$^{-1}$ (in illustrative embodiments, with carrier density up to $10^7$ cm$^{-3}$). In contrast, when the MRI machine 100 applies stimulus as described above, the conductivity of the doped GaAs of the semiconductor patch 810 increases to approximately 20 (ohm cm)$^{-1}$ (in illustrative embodiments, with carrier density up to 1018 cm$^{-3}$), resulting in the resonant frequency shift of the unit cell 301 described herein.

Taking a doped semiconductor patch 810 as an example, during transmission of RF energy by the MRI machine 100, the electric field at the gap of the BC-SRR 600 or inside the metallic helices 500 is very high, and so the carrier density of the doped silicon semiconductor patch 810 is excited to a much higher level than in the absence of such RF energy. In this state, the doped silicon semiconductor patch 810 can be treated as a conductor. Consequently, during transmission of RF energy by the MRI machine 100, the resonant frequency of the unit cells 301 deviates from the frequency of RF energy transmitted by the MRI machine 100.

In contrast, during reception by a unit cell 301 of RF signals from the patent 99—which occurs when the MRI machine 100 is not transmitting RF energy—the abovementioned electric field strength is much lower, and so the doped silicon semiconductor patch 810 is not an effective conductor. Consequently, the resonant frequency of each unit cell 301 remains aligned with the working frequency 452 of the MRI machine 100, as the doped silicon semiconductor patch 810 is functioning as an isolator.

The semiconductor patch 810 is disposed within the first gap 611 of the first SRR 610 in the BC-SRR 600, and changes its state in response to RF energy from the MRI machine 100. More specifically, in the absence of RF energy from the MRI machine 100, the semiconductor patch 810 is in the first state (high impedance), so the BC-SRR 600 behaves as described above in connection with FIGS. 6A-6E. When the MRI machine transmits RF energy, however, the semiconductor patch 810 changes its impedance to the second state (low impedance), thus electrically coupling the opposing ends 612, 612 of the first gap 611, thereby changing the physical and resonant characteristics of the BC-SRR 600, and thereby changing the operating characteristics of the array 300, as described above.

In some embodiments, each of the SRRs 610, 620 of a BC-SRR 600 includes a semiconductor patch 810 as described above, to even further change the characteristics of each unit cell 301 and of the array 300.

Figure 8C:
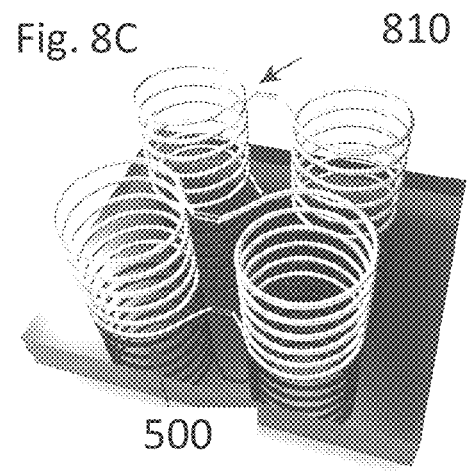

FIG. 8C schematically illustrates an array 300 of helical unit cells 500. In this embodiment, a semiconductor patch 810 is coupled between the respective ends 511 of adjacent unit cells 301, and preferably is disposed within the interior 802 if the helical coil itself—e.g., surrounded by the helical turns 513. In this configuration, in the absence of RF energy from the MRI machine 100, the semiconductor patch 810 is in the first state (high impedance), so the resonator 500 behaves as described above in connection with FIGS. 5A-5F. When the MRI machine transmits RF energy, however, the semiconductor patch 810 changes its impedance to the second state (low impedance), thus coupling together the adjacent unit cells 301, and thereby changing the operating characteristics of the array 300, as described above.

FIG. 8D and FIG. 8E schematically illustrate an alternate embodiment of a coupler 801, in which the coupler 801 is a switch 820, and alternate embodiments of arrays 300 with such couplers 801. Although the unit cells 301 in these embodiments respond to the control signal 821 (and therefore may be said to be in control communication with the MRI machine 100 or its controller 140), each of the arrays 300 may still be considered passive in that it does not require input of external energy in order to amplify the magnetic field and increase the SNR of signals from the specimen 99.

In FIG. 8D, at least one SRR 610 of each BC-SRR 600 has a switch 820 disposed in its gap 611. A control signal 821 from the MRI machine (e.g., from controller 140) changes the switch 820 between its first state (high impedance) and second state (low impedance), thus electrically coupling the opposing ends 612, 612 of the first gap 611. Those two states change the resonant characteristics of the BC-SRR 600, and thereby change the operating characteristics of the array 300, as described above in connection with FIG. 8B. In some embodiments, each of the SRRs 610, 620 of a BC-SRR 600 includes a switch 820 as described above, to even further change the characteristics of each unit cell 301 and of the array 300.

FIG. 8E schematically illustrates an array 300 of helical unit cells 500. In this embodiment, a switch 820 is coupled between the respective ends 511 of adjacent unit cells 301. A control signal 821 from the MRI machine changes the switch 820 between its first state (high impedance) and second state (low impedance). Those two states change the resonant characteristics of the helical cell 500, and thereby change the operating characteristics of the array 300, as described above in connection with FIG. 8C.

Figure 9:
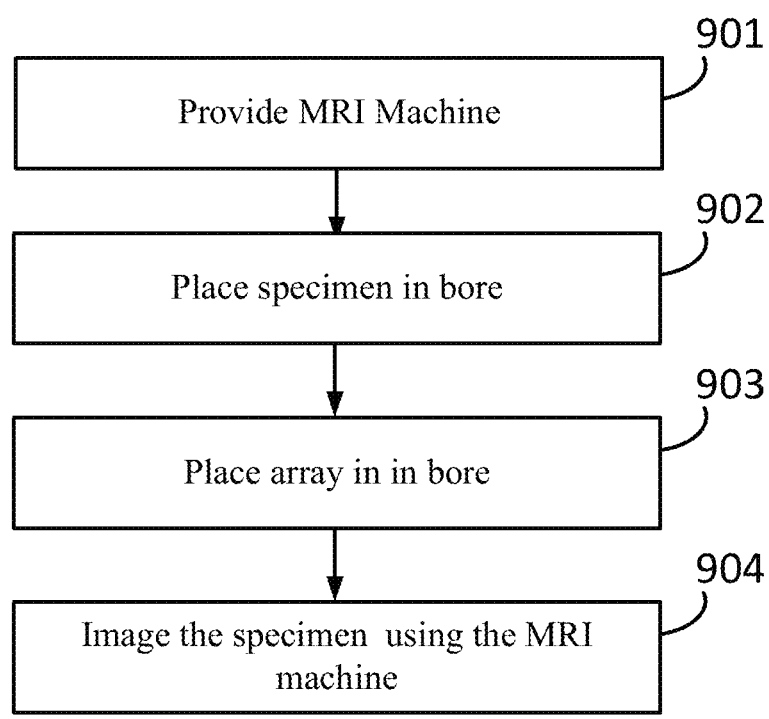
FIG. 9 is a flow chart for a method of imaging a specimen.

FIG. 9 is a flow chart for an embodiment of a method of magnetic resonant imaging a specimen 99. Step 901 requires providing an MRI machine 100 having a bore 102 and a working frequency. The MRI machine 100 may be, for example, a 1.5 Tesla MRI machine having a working frequency of 64 MHz or a 3 Tesla MRI machine having a working frequency of 128 MHz.

Step 902 includes placing the specimen in the bore 102, and step 903 includes placing, in the bore with the specimen, an array 300 of unit cells 301. It should be noted that steps 902 and 903 may be performed in any order with respect to one another.

In preferred embodiments, the array 300 is sized to be disposed within the bore 102 of the MRI machine 100 along with a specimen 99 in the bore 102, when the MRI machine 100 is imaging the specimen 99. For example, the array 300 of unit cells 301 may be any of the arrays 300 disclosed above.

In preferred embodiments, each unit cell 301 of the array 300 has a resonant frequency, and the array 300 has a resonance frequency at or near the working frequency of the MRI machine 100.

At step 904, the method images the specimen 99 with the MRI machine in ways known in the art.

In some embodiments, step 904 further includes controlling the coupler 801 to be in its first state (high-impedance) when the MRI machine is not applying electromagnetic (e.g., radio frequency) stimulus to the specimen 99, and to be in its second state (low impedance) when the MRI machine is applying such stimulus to the specimen. For example, if the coupler 801 is a switch 820, step 904 may include controlling the switch 820 with a control signal 821 from controller 140, as described above. As another example, if the coupler 801 is a semiconductor patch 810, step 904 may include controlling the semiconductor patch 810 to be in its first state (high-impedance) by withholding electromagnetic stimulus from the MRI machine 100, and controlling the semiconductor patch 810 to be in its second state (low-impedance) by applying electromagnetic stimulus from the MRI machine 100. In such embodiments, the coupler 801 is in a high-impedance state (and so the unit cells 301 resonate) when the MRI is not applying electromagnetic stimulus to the specimen, and the coupler 801 is in a low-impedance state (and so the unit cells 301 are effectively non-resonant) when the MRI is applying such electromagnetic stimulus to the specimen.

The following is a list of reference numbers used herein.
99: Specimen;
100: MRI machine in cross-section;
101: Table;
102: Bore of MRI machine;
110: Main field coils;
120: Body coils;
130: Specimen coils;
140: MRI machine controller;
150: Computer;
151: Computer communications link;
300: Resonator array;
301: Unit cell;
302: top of unit cell;
303: middle of unit cell;
310: X-Pitch;
311: Y-Pitch;
400: Response of a resonator;
401: Center frequency;
402: Upper 3 dB point;
403: Lower 3 dB point;
405: Noise level;
410: Frequency delta;
450: Frequency below working frequency of MRI machine;
452: Working frequency of MRI machine;
454: Frequency above working frequency of MRI machine;
460: Resonance response of array tuned to frequency below working frequency of MRI machine;
461: Resonant frequency of array tuned to frequency below working frequency of MRI machine;
462: Resonance response of array tuned to working frequency of MRI machine;
463: Resonant frequency of array tuned to working frequency of MRI machine;
464: Resonance response of array tuned to frequency above working frequency of MRI machine;
465: Resonant frequency of array tuned to frequency above working frequency of MRI machine;
500: Helical resonator;
501: Top end of resonator;
502: Bottom end of resonator;
503: Interior of resonator;
510: Conductor;
511: End of conductor;
512: Electrically insulating covering;
513: Turn;
515: Conductor gap;
520: Core;
521: Core outside diameter;
522: Core inside diameter;
523: Outer surface of core;
525: Core height;
530: Groove;
550: Additional reactance;
560: Dish;
561: Coupling loop;
565: Water;
566: Surface of water;
567: Dry resonant frequency;
568: 10% water resonant frequency;
569: 20% water resonant frequency;
600: BC-SRR resonator;
601: Top surface of BC-SRR;
602: Bottom surface of BC-SRR;
610: First split-ring resonator;
611: First gap;
612-613: Opposing ends of first gap;
620: Second split-ring resonator;
621: Second gap;
650: High-permittivity substrate;
700: Flexible substrate;
799: Limb of specimen;
801: Coupler;
802: Interior of helical coil;
810: Semiconductor patch;
820: Switch;

The embodiments of the inventions described above are intended to be merely exemplary; numerous variations and modifications will be apparent to those skilled in the art. All such variations and modifications are intended to be within the scope of the present invention as defined in any appended claims.

What is claimed is:

1. A passive apparatus for improving operation of an MRI machine characterized by a working frequency, by improving the signal-to-noise ratio of received signals, the apparatus comprising:
   an array of unit cells, the array sized to be disposed within a bore of the MRI machine along with a specimen in the bore, when the MRI machine is imaging the specimen, wherein:
   the unit cells are selected from the group consisting of broadside-coupled split-ring resonators, open loop coils, and helical coils,
   each unit cell has a resonant frequency, and
   the array has a resonance frequency at or near the working frequency,
   the unit cells configured such that they magnetically couple with one another,
   the array producing, in the signals emitted by the specimen and measured by the MRI machine, a signal-to-noise ratio of at least 50.

2. The apparatus of claim 1, wherein the unit cells are low-dielectric constant resonators.

3. The apparatus of claim 1, wherein each unit cell comprises a broadside-coupled split-ring resonator.

4. The apparatus of claim 3, wherein the array is configured such that its resonance frequency can be tuned by changing spacing between the unit cells.

5. The apparatus of claim 1, wherein the unit cells are open-loop coils.

6. The apparatus of claim 1, wherein the unit cells are helical coils separated from one another by a spacing, and the array is configured such that its resonance frequency can be tuned by changing the spacing between the helical coils.

7. The apparatus of claim 1, wherein the unit cells are configured to amplify the magnetic field of the signal, but not amplify the electric field of the signal.

8. The apparatus of claim 1, wherein the resonance frequency of the array is different from the working frequency of the MRI machine.

9. The apparatus of claim 1, wherein each unit cell comprises a coil having two ends, and each unit cell further comprises a capacitor electrically coupled between the two ends.

10. The apparatus of claim 1, wherein each unit cell comprises a coil having two ends, and each unit cell further comprises an inductor electrically coupled between the two ends.

11. The apparatus of claim 1, wherein each unit cell comprises:
a coil having two ends, and a coupler having a controllable variable impedance coupled between the two ends; each unit cell having a first resonant frequency when the coupler is in a first impedance state, and a second resonant frequency when the coupler is in a second impedance state.

12. The apparatus of claim 11, wherein the coupler is a semiconductor patch configured to change from the first impedance state to the second impedance state in response to RF energy transmitted by the MRI machine, to shift the resonant frequency of the unit cell away from the working frequency of the MRI machine such that the unit cell is effectively non-resonant.

13. The apparatus of claim 11, wherein the coupler is a switch configured to change from the first impedance state to the second impedance state in response to a signal from the MRI machine, to shift the resonant frequency of the unit cell away from the working frequency of the MRI machine.

14. The apparatus of claim 1, wherein the unit cell comprises:
a core; and
an open-loop coil wound around the core.

15. A method of magnetic resonance imaging a specimen, the method comprising:
providing an MRI machine having a bore and a working frequency;
placing the specimen within the bore;
placing, in the bore with the specimen, a passive array of unit cells, the array sized to be disposed within a bore of the MRI machine along with a specimen in the bore, when the MRI machine is imaging the specimen, wherein:
the unit cells are selected from the group consisting of broadside-coupled split-ring resonators, open loop coils, and helical coils;
each unit cell has a resonant frequency, and
the array has a resonance frequency at or near the working frequency, operating the MRI machine to image the specimen.

16. The method of claim 15, wherein the MRI machine is one of:
(A) a 1.5 Tesla MRI machine having a working frequency of 64 MHz, and the resonance frequency of the array is within 5 percent of 64 MHz; or
(B) a 3 Tesla MRI machine having a working frequency of 128 MHz, and the resonance frequency of the array is within 5 percent of 128 MHz.

17. A passive apparatus for improving operation of an MRI machine having a bore and characterized by a working frequency, by improving the signal-to-noise ratio of received signals, the apparatus comprising:
an array of unit cells, the array sized to fit within the bore of an MRI machine;
each unit cell comprising means for resonating, said means selected from the group consisting of broadside-coupled split-ring resonators, open loop coils, and helical coils; and
the array has a resonance frequency at the working frequency of the MRI machine,
the unit cells disposed such that they magnetically couple with one another,
the array producing, in the signals measured by the MRI machine, a signal-to-noise ratio of at least 50.

18. The apparatus of claim 17, wherein the means for resonating comprises an open-loop helical resonator.

19. The apparatus of claim 18 wherein the open-loop helical resonator comprises a coil having two ends, and a coupler having a controllable variable impedance coupled between the two ends, each unit cell having a first resonant frequency when the coupler is in a first impedance state, and a second resonant frequency when the coupler is in a second impedance state.

20. The apparatus of claim 17, wherein the means for resonating comprises a broadside-coupled split ring resonator.

* * * * *